(12) United States Patent
Singh et al.

(10) Patent No.: US 11,033,889 B2
(45) Date of Patent: Jun. 15, 2021

(54) PALLADIUM ACYCLIC DIAMINOCARBENE COMPLEXES AS PRECATALYSTS FOR HIYAMA COUPLING AND THE TANDEM ONE-POT FLUORIDE FREE HIYAMA COUPLING/CYCLIZATION FOR THE SYNTHESIS OF BIOLOGICALLY RELEVANT

(71) Applicant: INDIAN INSTITUTE OF TECHNOLOGY BOMBAY, Mumbai (IN)

(72) Inventors: Chandan Singh, Mumbai (IN); Prasenjit Ghosh, Mumbai (IN)

(73) Assignee: INDIAN INSTITUTE OF TECHNOLOGY BOMBAY, Mumbai (IN)

( * ) Notice: Subject to any disclaimer, the term of this patent is extended or adjusted under 35 U.S.C. 154(b) by 192 days.

(21) Appl. No.: 16/168,434

(22) Filed: Oct. 23, 2018

(65) Prior Publication Data
US 2020/0122132 A1    Apr. 23, 2020

(51) Int. Cl.
*B01J 31/22*    (2006.01)
*C07D 307/79*    (2006.01)

(52) U.S. Cl.
CPC ........ *B01J 31/2278* (2013.01); *C07D 307/79* (2013.01); *B01J 2231/4205* (2013.01); *B01J 2531/824* (2013.01)

(58) Field of Classification Search
CPC .................................................. B01J 31/2278
See application file for complete search history.

(56) References Cited

U.S. PATENT DOCUMENTS

2012/0108819 A1* 5/2012 Hashmi ................ C07F 15/006
548/103

OTHER PUBLICATIONS

Anisimova, T. B.; Guedes da Silva, M. F. C.; Kukushkin, V. Y.; Pombeiro, A. J. L.; Luzyanin, K. V. Dalton Trans. 2014, 43, 15861 "Metal-mediated coupling of amino acid esters with isocyanides leading to new chiral acyclic aminocarbene complexes" (Year: 2014).*

M. A. Kinzhalov, G. L. Starova and V. P. Boyarskiy, Inorg. Chim. Acta, 2017, 455, 607-612 "Interaction of benzene-1,2-diamines with isocyanide complexes of palladium(II): Insight into the mechanism" (Year: 2017).*

Singh, Chandan; Prakasham, A. P.; Gangwar, Manoj Kumar; Butcher, Raymond J.; Ghosh, Prasenjit (2018): One-Pot Tandem Hiyama Alkynylation/Cyclizations by Palladium(II) Acyclic Diaminocarbene (ADC) Complexes Yielding Biologically Relevant Benzofuran Scaffolds. ACS Omega 2018, 3, 1740-1756. DOI: 10.1021/acsomega.7b01974.

* cited by examiner

*Primary Examiner* — Yun Qian
(74) *Attorney, Agent, or Firm* — Volpe Koenig

(57) ABSTRACT

The present invention provides Acyclic diaminocarbene complex of formula (I):

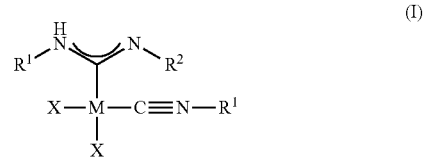

Wherein,
M is palladium;
X is monoanionic ligand selected from Cl, Br or I;
Where R1 is different from R2;
R1 is selected from the group consisting of alkyl or aryl, each of which have 4 to 20 carbon atoms, and may optionally contain one or more heteroatoms;
R2 is selected from the group consisting of alkyl, or aryl each of which have 4 to 20 carbon atoms, and may optionally contain one or more heteroatoms. The said palladium diamino carbine complex of the present invention are particularly useful as catalyst from Hiyama cross-coupling reaction.

5 Claims, 1 Drawing Sheet

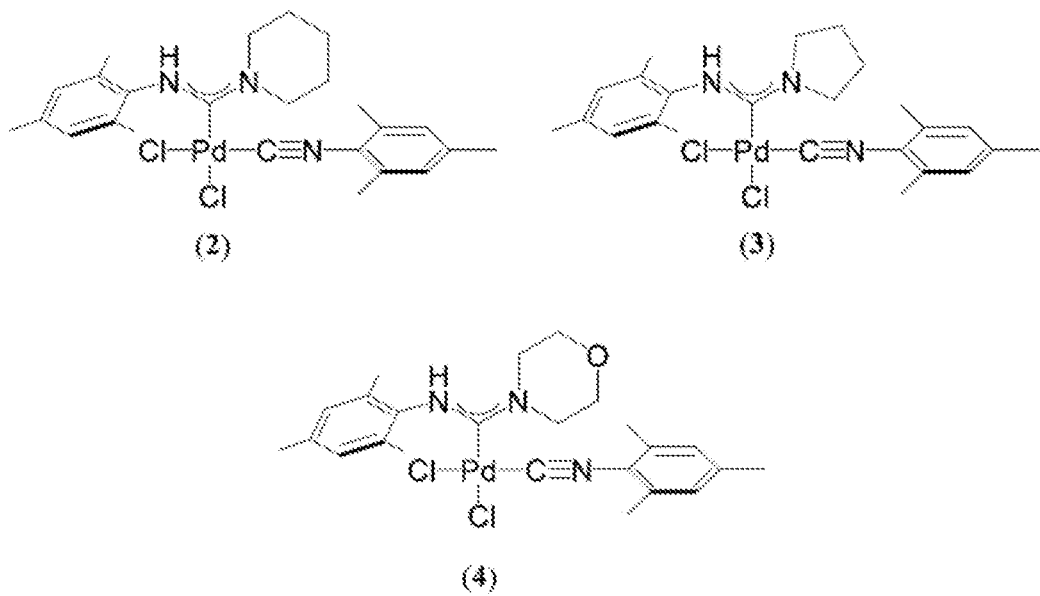

PALLADIUM ACYCLIC DIAMINOCARBENE COMPLEXES AS PRECATALYSTS FOR HIYAMA COUPLING AND THE TANDEM ONE-POT FLUORIDE FREE HIYAMA COUPLING/CYCLIZATION FOR THE SYNTHESIS OF BIOLOGICALLY RELEVANT

FIELD OF INVENTION

The present invention reports a series of palladium acyclic diaminocarbene (ADC) complexes, particularly to the compounds of the formulation cis-[(R1NH)(R2)methylidene]PdCl2(CNR1) [R1=2,4,6-(CH3)3C6H2; R2=NC5H10 (2); NC4H8 (3); NC4H8O (4)] and represented by Formula (I) and acts as metal catalyst for the organic synthesis reactions particularly for Hiyama coupling and for Csp2-Csp type Hiyama coupling followed by cyclization of reactions.

Formula (I)

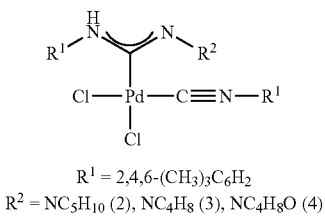

$R^1$ = 2,4,6-(CH$_3$)$_3$C$_6$H$_2$
$R^2$ = NC$_5$H$_{10}$ (2), NC$_4$H$_8$ (3), NC$_4$H$_8$O (4)

BACKGROUND AND PRIOR ART OF INVENTION

Singh, C. et al. "One-Pot Tandem Hiyama Alkynylation/Cyclizations by Palladium(II) Acyclic Diaminocarbene (ADC) Complexes Yielding Biologically Relevant Benzofuran Scaffolds" (2018) ACS Omega 3 (2): 1740-1756 was authored by the inventors Prasenjit Ghosh and Chandan Singh and by A. P. Prakasham, Manoj K. Gangwar and Raymond J. Butcher. The authors A. P. Prakasham, Manoj K. Gangwar and Raymond J. Butcher contributed X-ray crystallographic characterization data in [ACS Omega 2018:3: 1740-1756]. To the extent that the disclosure of [ACS Omega 2018:3:1740-1756] overlaps with the subject matter of this application, it was by one or both of the inventors or by another who obtained the subject matter disclosed directly or indirectly from one or both of the named inventors.

The benzofuran compounds are important building blocks for biologically active molecules viz. BNC105 (Flynn, B. L.; Gill, G. S.; Grobelny, D. W.; Chaplin, J. H.; Paul, D.; Leske, A. F.; Lavranos, T. C.; Chalmers, D. K.; Charman, S. A.; Kostewicz, E.; Shackleford, D. M.; Morizzi, J.; Hamel, E.; Jung, M. K.; Kremmidiotis, G., J. Med. Chem. 2011, 54, 6014-6027), amiodarone (Singh, S. N.; Fletcher, R. D.; Fisher, S. G.; Singh, B. N.; Lewis, H. D.; Deedwania, P. C.; Massie, B. M.; Colling, C.; Lazzeri, D., N. Engl. J. Med. 1995, 333, 77-82), cytotoxic flavonoids (Shi, Y.-Q.; Fukai, T.; Sakagami, H.; Chang, W.-J.; Yang, P.-Q.; Wang, F.-P.; Nomura, T., J. Nat. Prod. 2001, 64, 181-188) and natural products like, Daphnodorin A and B (Yuan, H.; Bi, K.-J.; Li, B.; Yue, R.-C.; Ye, J.; Shen, Y.-H.; Shan, L.; Jin, H.-Z.; Sun, Q.-Y.; Zhang, W.-D., Org. Lett. 2013, 15, 4742-4745), Egonol (Naveen, M.; Reddy, C. U.; Hussain, M. M.; Chaitanya, M.; Narayanaswamy, G., J. Heterocycl. Chem. 2013, 50, 1064-1066; Choi, D. H.; Hwang, J. W.; Lee, H. S.; Yang, D. M.; Jun, J.-G., Bull. Korean Chem. Soc. 2008, 29, 1594-1596) and Moracin O and P (Xia, Y.; Jin, Y.; Kaur, N.; Choi, Y.; Lee, K., Eur. J. Med. Chem. 2011, 46, 2386-2396; Kaur, N.; Xia, Y.; Jin, Y.; Dat, N. T.; Gajulapati, K.; Choi, Y.; Hong, Y.-S.; Lee, J. J.; Lee, K., Chem. Commun. 2009, 1879-1881), and consequently its synthesis by an efficient route is of considerable interest (Agasti, S.; Dey, A.; Maiti, D., Chem. Commun. 2017, 53, 6544-6556; Blanc, A.; Bénéteau, V.; Weibel, J.-M.; Pale, P., Org. Biomol. Chem. 2016, 14, 9184-9205;).

In this context, the benzofuran derivatives has been successfully synthesized by different-different synthetic strategies (Geary, L. M.; Hultin, P. G., Org. Lett. 2009, 11, 5478-5481; Yin, S.-C.; Zhou, Q.; Zhao, X.-Y.; Shao, L.-X., J. Org. Chem. 2015, 80, 8916-8921), of these, the one-pot tandem C—C bond coupling/cyclization reactions (Bosiak, M. J. ACS Catal. 2016, 6, 2429-2434; Kumar, A.; Gangwar, M. K.; Prakasham, A. P.; Mhatre, D.; Kalita, A. C.; Ghosh, P. Inorg. Chem. 2016, 55, 2882-2893), for producing benzofuran derivative, provides a convenient and time efficient divert synthetic approach.

The first part of this invention includes the C—C coupling by means of the Hiyama coupling. The Hiyama coupling is important primarily for the reason that (i) it provides a much greener alternative to the Suzuki and Stille coupling having toxicity issues (ii) until now the Hiyama coupling has not been reported for the transition metal acyclic diaminocarbene (ADC) complexes (Boyarskiy, V. P.; Luzyanin, K. V.; Kukushkin, V. Y. Coord. Chem. Rev. 2012, 256, 2029-2056; Slaughter, L. M. ACS Catal. 2012, 2, 1802-1816;). The second part of the invention leads with utility of transition metal acyclic diaminocarbene complexes for one-pot tandem Hiyama coupling/cyclization reaction for producing benzofuran derivatives.

Till the date N-heterocyclic carbene (NHC) complexes has proved to be very good and effective catalysts in homogeneous catalysis (Nasr, A.; Winkler, A.; Tamm, M., Coord. Chem. Rev. 2016, 316, 68-124; Nolan, S. P., Chem. Soc. Rev. 2011, 40, 5151-5169), however their application in more challenging areas of catalysis like bifunctional catalysis (Ramasamy, B.; Ghosh, P., Eur. J. Inorg. Chem. 2016, 2016, 1448-1465), asymmetric catalysis (Janssen-Müller, D.; Schlepphorst, C.; Glorius, F., Chem. Soc. Rev. 2017, 46, 4845-4854) and tandem reaction (Nolan, S. P.; Clavier, H., Chem. Soc. Rev. 2010, 39, 3305-3316) are much warranted. Alongside, an arduous search for discovering different variants of the carbene ligands is being pursued for their potential application in chemical catalysis. In this regard a special class of heteroatom stabilized singlet carbene ligand in the form of the acyclic diaminocarbenes (ADC) is noteworthy (Boyarskiy, V. P.; Luzyanin, K. V.; Kukushkin, V. Y., Coord. Chem. Rev. 2012, 256, 2029-2056; Slaughter, L. M., ACS Catal. 2012, 2, 1802-1816) preparation particularly for their ease of as compared to preparations of the contemporary phosphine and the N-heterocyclic carbene (NHC) ligands. Additionally, acyclic diaminocarbenes (ADC) ligands are free of geometric constraints that lead to free orientation even the bulkier ligand substituents around carbene center. This differentiates the acyclic diaminocarbenes (ADC) ligands from their cyclic counterparts namely, the N-heterocyclic carbene (NHC) ligands, not only structurally but also in exhibiting different catalytic properties.

The present invention demonstrating the utility of transition metal acyclic diaminocarbenes (ADC) complexes in Hiyama coupling reactions and also in another subsequent application involving the one-pot tandem Hiyama coupling/cyclization reaction.

The known reports of the application of palladium acyclic diaminocarbene complexes mainly been used in Suzuki coupling (Luzyanin, K. V.; Tskhovrebov, A. G.; Carias, M. C.; Guedes da Silva, M. F. C.; Pombeiro, A. J. L.; Kukushkin, V. Y. Organometallics 2009, 28, 6559-6566; Kinzhalov, M. A.; Luzyanin, K. V.; Boyarskiy, V. P.; Haukka, M.; Kukushkin, V. Y. Organometallics 2013, 32, 5212-5223; Hashmi, A. S. K.; Lothschűutz, C.; Bőhling, C.; Rominger, F. Organometallics 2011, 30, 2411-2417) and Sonogashira coupling (Timofeeva, S. A.; Kinzhalov, M. A.; Valishina, E. A.; Luzyanin, K. V.; Boyarskiy V. P.; Buslaeva, T. M.; Haukka M; Kukushkin, V. Y. J. Catal. 2015, 329, 449-456; Valishina, E. A.; Guedes da Silva, M. F. C.; Kinzhalov, M. A.; Timofeeva, S. A.; Buslaeva, T. M; Haukka M; Pombeiro, A. J. L.; Boyarskiy V. P.; Kukushkin, V. Y.; Luzyanin, K. V. J. Mol. Catal. A.: Chemical 2014, 395, 162-171; Mikhaylov, V. N.; Sorokoumov, V. N.; Korvinson, K. A.; Novikov, A. S.; Balova, I. A. Organometallics 2016, 35, 1684-1697;). In absence of any report on Hiyama coupling as well as their application in tandem reaction we became interested in the same.

OBJECTIVE OF THE INVENTION

It is an object of the present invention to overcome the drawbacks of the prior art.

It is another object of the present invention to provide a series of palladium acyclic diaminocarbene (Pd-ADC) metal complex of general formula (I) above, having catalytic activity in Hiyama coupling reaction of Csp2-Csp type reactions.

It is another object of the present invention having catalytic activity in Csp2-Csp type Hiyama coupling followed by cyclization reactions.

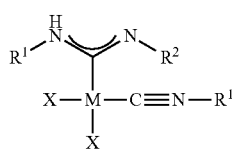

(I)

It is another object of the present invention to provide palladium acyclic diaminocarbene (Pd-ADC) metal complexes of particular formulation cis-[(2,4,6-(CH3)3C6H2NH)(R)methylidene]PdX2(CN-2,4,6-(CH3)3C6H2) where R=NC5H10, NC4H8, NC4H8O; X=Cl, represented by formula (I) below:

Formula (I)

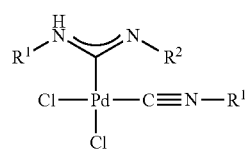

$R^1$ = 2,4,6-(CH$_3$)$_3$C$_6$H$_2$
$R^2$ = NC$_5$H$_{10}$ (2), NC$_4$H$_8$ (3), NC$_4$H$_8$O (4)

It is another object of the present invention to provide a catalytic activity catalyzed by present (ADC)MX2(CN-2,4,6-(CH3)3C6H2) (wherein, M is Pd, X is Cl) type metal complexes of general formula (I) above in Hiyama coupling reaction of aryl iodide/bromide and triethoxysilylalkynes.

It is another object of the present invention to provide a catalytic activity catalyzed by present (ADC)MX2(CN-2,4,6-(CH3)3C6H2) (wherein, M is Pd, X is Cl) type metal complexes of general formula (I) above in Hiyama coupling/cyclization reaction of iodo/bromo-phenol and triethoxysilylalkynes to obtain benzofuran compounds.

It is another object of the present invention to provide mode of action and mechanistic insights on the catalysis process of the formation of Hiyama coupling products and the benzofuran product of cyclization process.

SUMMARY OF THE INVENTION

An aspect of the present invention provides an acyclic diaminocarbene complex of formula (I):

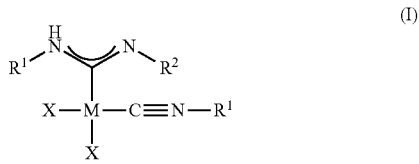

(I)

wherein,
M is palladium;
X is a monoanionic ligand selected from Cl, Br or I;
Where R1 is different from R2. R1 and R2 are independently selected from C1-10alkyl, C2-10alkenyl, C2-10alkynyl, C3-10cycloalkyl, heteroaryl and aryl, each group being optionally substituted or R2 represents a ring having nitrogen atom attached to it, an optionally substituted monocyclic or polycyclic, saturated or unsaturated ring system that contains 4 to 30 carbon atoms of which one or more of the carbon atoms is optionally replaced with a hetero-moiety selected from O, S, NH and NC1-6alkyl.

Another aspect of the present invention provides a process for preparation of the palladium acyclic diaminocarbene (Pd-ADC) metal complexes of the present invention which comprises steps of: (1) converting an aniline derivative to N-formamide using formic acid and acetic anhydride; followed by a (2) formation of isocyanide compound by using POCl3 and triethyl amine as a suitable base with reaction of hydrocarbyl formed in step '1'; (3) metallation of the compound formed in step '2' with the reaction of (CH3CN)2PdCl2 to give respective palladium metal precursor; (4) directly reacting the formed palladium metal precursor with different cyclic secondary amine, wherein M is Pd, X is a monoanionic ligand selected from Br, Cl, or I, at room temperature formed the proposed metal complex.

The catalysts of the present disclosure facilitate chemical reaction for C—C bond formation, particularly of Csp2-Csp type Hiyama coupling.

The palladium acyclic diaminocarbene (Pd-ADC) metal complexes of present invention act as catalysts to facilitate chemical reaction for carbon-carbon bond formation, particularly of Csp2-Csp type Hiyama coupling followed by cyclization to provide the time efficient one-pot reaction for the formation of biologically active benzofuran compounds.

BRIEF DESCRIPTION OF ACCOMPANYING DRAWINGS

FIG. 1 show certain specific catalysts representing individual embodiments of the present disclosure and shows structures of palladium acyclic diaminocarbene (ADC) complexes.

DETAILED DESCRIPTION OF INVENTION

The following description with reference to the accompanying drawings is provided to assist in a comprehensive understanding of exemplary embodiments of the invention. It includes various specific details to assist in that understanding but these are to be regarded as merely exemplary.

Singh, C. et al. [ACS Omega 2018: 3: 1740-1756] is incorporated herein by reference as if fully set forth.

Accordingly, those of ordinary skill in the art will recognize that various changes and modifications of the embodiments described herein can be made without departing from the scope of the invention. In addition, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, integers, steps or components but does not preclude the presence or addition of one or more other features, integers, steps, components or groups thereof.

Compounds of this invention can exist as one or more stereoisomer. The various stereoisomers include diastereomers and geometric isomers. Accordingly, the present invention comprises mixtures, individual stereoisomers of compounds of Formulae (I).

The term 'ADC' as used herein refers to Acyclic diaminocarbene ligands, accordingly the term Pd-ADC as used herein refers to palladium acyclic diaminocarbene complexes.

The term "alkyl" as used herein includes straight-chain or branched alkyl, such as, methyl, ethyl, n-propyl, i-propyl, or the different butyl, pentyl, hexyl, heptyl, octyl, nonyl, or decyl isomers.

The term "monoanionic ligand" as used herein, includes chlorine, bromine and iodine.

The term "hydrocarbyl" as used herein includes organic substituents primarily composed of carbon and hydrogen which may be aliphatic, alicyclic, aromatic or combinations thereof, e.g., aralkyl or alkaryl. Such hydrocarbyl groups may also contain aliphatic unsaturation, i.e., olefinic or acetylenic unsaturation.

The term "aryl/aromatic ring system" as used herein includes phenyl which may be optionally substituted by up to five substituents. Suitable substituents include halogen, (C1-6)alkyl, aryl(C1-6)alkyl, (C1-6)alkoxy, (C1-6)alkoxy(C1-6)alkyl, halo(C1-6)alkyl, hydroxy, nitro, amino, carboxy, carboxy salts, carboxy esters, carbamoyl, (C1-6)alkoxycarbonyl, heterocyclyl and heterocyclyl(C1-6)alkyl. In addition, the term "aryl" may also include single and fused rings, of which at least one is aromatic, which rings may be unsubstituted or substituted by, for example, up to three substituents as set out above.

The term "heterocyclyl ring system" as used herein includes any monocyclic or polycyclic aromatic or aliphatic ring system ring system having one or more heteroatoms such as, but not limited to, nitrogen, oxygen, or sulphur. The total number of carbon atoms in a substituent group is designated by a range of "C1-C10" indicating carbon numbers from 1 to 10. For example, C1-C3 alkyl designates methyl through propyl, and C4 alkyl designates the various isomers of an alkyl group containing a total of 4 carbon atoms.

The term "L2MX2" broadly includes (CH3CN)2PdCl2, PdCl2, PdBr2, PdI2, Pd(OCOCH3)2 and Pd(OCOCF3)2.

Important are the compounds their enantiomeric forms or methods or schemes or processes described below, wherein, M is palladium (Pd); X is a monoanionic ligand selected from Cl, Br or I;

R1 is substituted or unsubstituted hydrocarbyl selected from 2,4,6-(CH3)3C6H2,1-cyclohexyl, 2,6-{(CH3)2CH}2C6H3, C1-C10 alkyl, aryl, heterocyclyl, allyl, alkylheterocyclyl.

R2 is selected from a group consisting of C1-C10 alkyl, aryl, heterocyclyl, allyl, alkylheterocyclyl.

The present invention provides palladium acyclic diaminocarbene (Pd-ADC) complexes of type (ADC)PdX2 (CN-2,4,6-(CH3)3C6H2) (wherein X is monoanionic ligands) for exhibiting catalytic activity in Hiyama coupling reaction of Csp2-Csp type.

The present invention provides palladium acyclic diaminocarbene (Pd-ADC) complexes of type (ADC)PdX2 (CN-2,4,6-(CH3)3C6H2) (wherein X is monoanionic ligands) for exhibiting catalytic activity in Csp2-Csp type Hiyama coupling followed by cyclization reaction to provide benzofuran compounds.

An embodiment of the present invention provides a palladium acyclic diaminocarbene (Pd-ADC) metal complex of general formula (I):

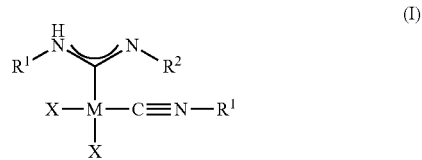

In accordance with the present invention, palladium acyclic diaminocarbene complexes of formula (I) used in the Hiyama coupling reaction of Csp2-Csp type and also for Csp2-Csp type Hiyama coupling followed by cyclization reaction of above formula (I), the transition metal (M) is palladium (Pd). Where R1 is different from R2. R1 is selected from the group consisting of alkyl or aryl, each of which have 4 to 20 carbon atoms, and may optionally contain one or more heteroatoms; R2 is selected from the group consisting of alkyl, or aryl each of which have 4 to 20 carbon atoms, and may optionally contain one or more heteroatoms; X is selected from the group consisting of halides which can be Cl, Br or I.

Representative examples of the present palladium acyclic diaminocarbene (Pd-ADC) complex are:

(i). cis-[(2,4,6-(CH3)3C6H2NH)(NC5H10)methylidene] PdCl2(CN-2,4,6-(CH3)3C6H2) having formula (Ia):

Formula (Ia)

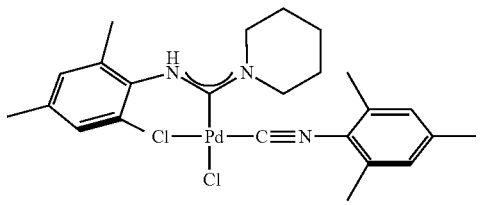

(ii). cis-[(2,4,6-(CH3)3C6H2NH)(NC4H8)methylidene] PdCl2(CN-2,4,6-(CH3)3C6H2) having formula (Ib):

Formula (Ib)

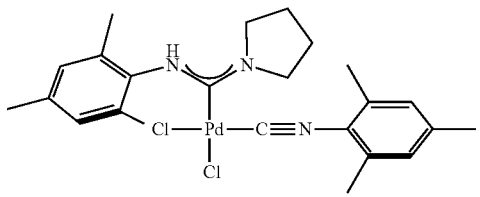

(iii). cis-[(2,4,6-(CH3)3C6H2NH)(NC4H8O)methylidene] PdCl2(CN-2,4,6-(CH3)3C6H2) having formula (Ic):

Formula (Ic)

(4)

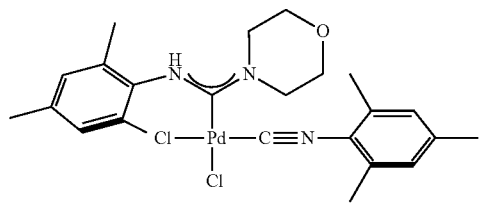

The present invention thus provides the compounds of formula (Ia, Ib, and Ic) as mentioned above, which are found to be effective for the Hiyama coupling reaction of Csp2-Csp type and also for Csp2-Csp type Hiyama coupling followed by cyclization reaction.

Another aspect of the present invention provides a process for preparation of the palladium acyclic diaminocarbene (Pd-ADC) metal complexes of the present invention which comprises steps of: (1) converting an amine derivative to N-formamide using formic acid and acetic anhydride; followed by a (2) formation of isocyanide compound by using POCl3 and triethyl amine as a suitable base with reaction of hydrocarbyl formed in step '1'; (3) metallation of the compound formed in step '2' with the reaction of L2MX2 to give respective palladium metal precursor; (4) directly reacting the formed palladium metal precursor with different cyclic secondary amine, wherein M is Pd, X is a monoanionic ligand selected from Br, Cl, or I, at room temperature formed. The said process is represented by the following general scheme 1:

The current invention involves the synthesis of Pd-ADC complexes using different type of secondary amines. In particular, there is no example of the variation of primary aromatic amine and the cyclic secondary amines that have been reported for the synthesis of Pd-ADC complexes. Accordingly the present inventors have achieved the synthesis of cyclic secondary amines along with 2,4,6-trimethyl aniline.

Scheme 1

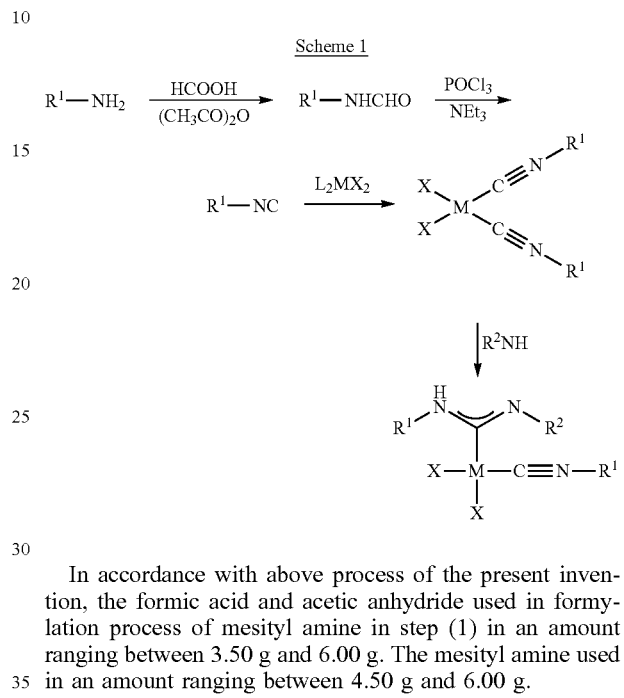

In accordance with above process of the present invention, the formic acid and acetic anhydride used in formylation process of mesityl amine in step (1) in an amount ranging between 3.50 g and 6.00 g. The mesityl amine used in an amount ranging between 4.50 g and 6.00 g.

In step (2) POCl3 and base; NEt3 is used for making isocyanides from the product of step (1), and is using in the range between 3.00 g and 7.00 g. In step (3) from isocyanides metal precursor has been prepared by using (MeCN)2PdCl2 and used in the range between 0.100 g and 0.500 g. The secondary amine used in step (4) may use piperidene, pyrrolidene and morpholine and is used in an amount ranging between 0.010 g and 0.100 g. Therefore, the present Pd-ADC compounds of formula (Ia to Ic) are prepared by the above process of scheme 1.

Another embodiment of the present invention provides a catalytic activity of Pd-ADC metal complexes in (i) Hiyama coupling reaction of Csp2-Csp type, between aryl iodide and triethoxysilylalkyne (ii). Csp2-Csp type Hiyama coupling followed by cyclization reaction between iodophenol and triethoxysilylalkyne.

The representative examples of Pd-ADC compounds in present catalytic activity are chosen from one or more of:
(i). cis-[(2,4,6-(CH3)3C6H2NH)(NC5H10)methylidene] PdCl2(CN-2,4,6-(CH3)3C6H2) having formula (Ia);
(ii). cis-[(2,4,6-(CH3)3C6H2NH)(NC4H8)methylidene] PdCl2(CN-2,4,6-(CH3)3C6H2) having formula (Ib);
(iii). cis-[(2,4,6-(CH3)3C6H2NH)(NC4H8O)methylidene] PdCl2(CN-2,4,6-(CH3)3C6H2) having formula (Ic).

The present invention also comprises a method of acting metal-catalyzed organic synthesis reactions containing contacting substrates for the organic synthesis reaction with a metal catalyst of the formula (I) as defined above under conditions for acting the organic synthesis reaction, and optionally isolating one or more products from the organic synthesis reaction. In an embodiment of the disclosure, the organic synthesis reaction is any reaction that benefits from the presence or use of a metal catalyst, for example, but not limited to, conjugate additions, hydrogenations, hydrosilations and cross-couplings.

In an embodiment of the disclosure, the organic synthesis conversion is a C—C bond coupling reaction of the Csp2-Csp type catalyzed by present acyclic diaminocarbene complex of the present invention, in which (i). Hiyama coupling reaction of Csp2-Csp type between aryl iodide and triethoxysilylalkyne and (ii). Csp2-Csp type Hiyama coupling followed by cyclization reaction of between iodophenol and triethoxysilylalkyne.

The present invention provides a catalytic activity comprising Pd-ADC compound, (ADC)PdX2(CN-2,4,6-(CH3)3C6H2) (wherein X is monoanionic ligands) (ADC=[(2,4,6-(CH3)3C6H2NH)(NC5H10)methylidene] of general formula (Ia), [(2,4,6-(CH3)3C6H2NH)(NC4H8)methylidene] of general formula (Ib) and [(2,4,6-(CH3)3C6H2NH)(NC4H8O)methylidene] of general formula (Ic) which is used to study the catalytic activity in (i) Hiyama coupling reaction of Csp2-Csp type, between aryl iodide and triethoxysilylalkyne (ii). Csp2-Csp type Hiyama coupling followed by cyclization reaction between iodophenol and triethoxysilylalkyne.

These series of palladium acyclic diaminocarbene complexes (formula Ia-Ic) of the present invention are found to exhibit catalytic activity in the Csp2-Csp type Hiyama coupling as well as in Csp2-Csp type of Hiyama coupling/cyclization reactions. The most catalytic active compound in these reactions are complex 4 of the general formula Ic and higher yield reported in both the cases with aromatic triethoxysilylalkynes. With aliphatic triethoxysilylalkynes the yields are poor. There are significant improvement in yield of catalytic product has been observed when compared the yield of reaction catalyzed by PdCl2 and Cl2Pd(MeCN)2. Hg-drop test for homogeneity yielded almost equal yield.

EXAMPLES

The present disclosure may be better understood through reference to the 10 following examples. These examples are included to describe exemplary embodiments only and should not be interpreted to encompass the entire breadth of the invention.

Scheme 2

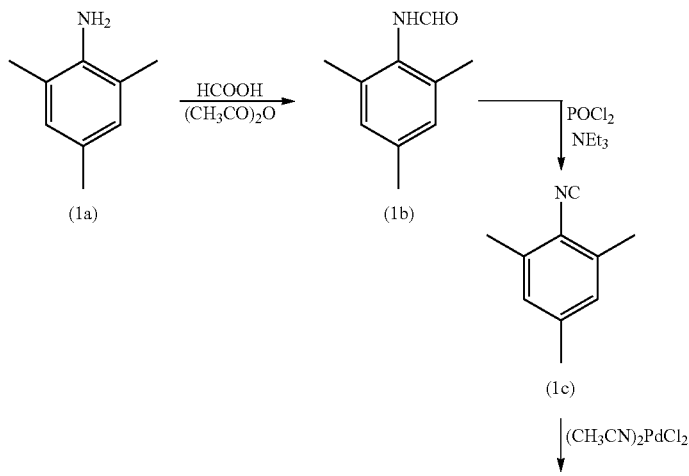

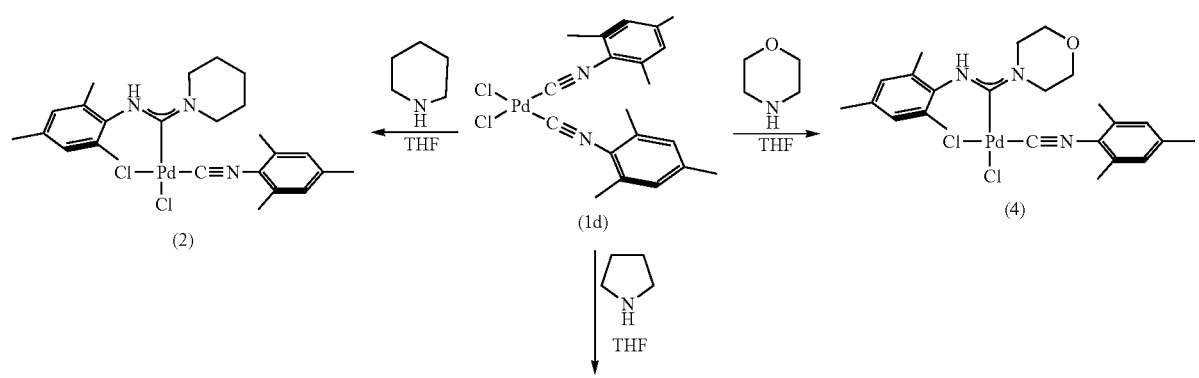

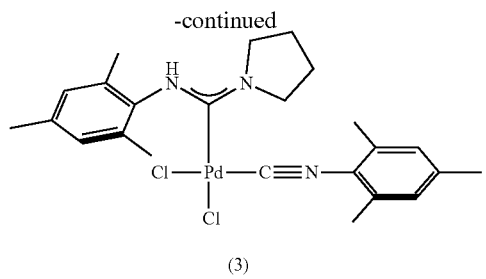

(3)

Example 1

Synthesis of cis-[((2,4,6-trimethylphenylamino)(piperidin-1-yl)methylidene)] PdCl2 (2,4,6-trimethylphenylisonitrile) (2)

To a solution of cis-{(2,4,6-(CH3)3C6H2)NC}2PdCl2 (Id) (0.176 g, 0.376 mmol) in THF (ca. 10 mL) at 0° C., piperidine (0.032 g, 0.376 mmol) was added and the reaction mixture was stirred overnight at room temperature. The solvent was then removed under reduced pressure and the residue so obtained was purified by column chromatography using silica gel as a stationary phase and by eluting with a CHCl3/CH3OH mixture (95:5 v/v) to give the product (2) as an yellow solid (0.138 g, 66%).

Formula (Ia)

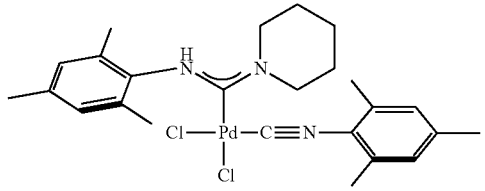

(2)

Yield: 66%
Spectral Data:
1H NMR, (DMSO-d6, 400 MHz, 25° C.): δ 9.07 (s, 1H, NH), 7.09 (s, 2H, 2,4,6-(CH3)3C6H2), 7.00 (s, 1H, 2,4,6-(CH3)3C6H2), 6.77 (s, 1H, 2,4,6-(CH3)3C6H2), 4.57 (br, 1H, NC5H10), 4.28 (br, 1H, NC5H10), 3.86 (br, 2H, NC5H10), 2.39 (s, 3H, 2,4,6-(CH3)3C6H2), 2.28 (s, 3H, 2,4,6-(CH3)3C6H2), 2.25 (s, 3H, 2,4,6-(CH3)3C6H2), 2.21 (s, 6H, 2,4,6-(CH3)3C6H2), 1.93 (s, 3H, 2,4,6-(CH3)3C6H2), 1.72-1.54 (m, 6H, NC5H10). 13C NMR (DMSO-d6, 125 MHz, 25° C.): δ 179.9 (NHCN), 140.8 (2,4,6-(CH3)3C6H2), 137.4 (2,4,6-(CH3)3C6H2), 137.3 (2,4,6-(CH3)3C6H2), 135.4 (2,4,6-(CH3)3C6H2), 135.2 (2,4,6-(CH3)3C6H2), 135.0 (2,4,6-(CH3)3C6H2), 134.9 (2,4,6-(CH3)3C6H2), 134.3 (2,4,6-(CH3)3C6H2), 129.7 (2,4,6-(CH3)3C6H2), 129.1 (2,4,6-(CH3)3C6H2), 129.1 (2,4,6-(CH3)3C6H2), 128.5 (2,4,6-(CH3)3C6H2), 122.7 (CN-2,4,6-(CH3)3C6H2), 56.6 (NC5H10), 47.6 (NC5H10), 26.2 (NC5H10), 26.1 (NC5H10), 23.6 (NC5H10), 21.0 (2,4,6-(CH3)3C6H2), 20.7 (2,4,6-(CH3)3C6H2), 19.6 (2,4,6-(CH3)3C6H2), 18.2 (2,4,6-(CH3)3C6H2), 17.9 {2(2,4,6-(CH3)3C6H2)}. IR data (KBr pellet): 3249 (s), 2924 (s), 2198 (s), 1608 (w), 1560 (s), 1443 (w), 1342 (w), 1247 (w), 1023 (w) 855 (w), 655 (w) cm-1. HRMS Calcd. For [C25H33N3Cl2Pd—Cl]+518.1389, found m/z 518.1389.

Anal. Calcd. for C25H33Cl2N3Pd: C, 54.31, H, 6.02, N, 7.60%. Found: C, 54.47, H, 5.67, N, 7.11%.

Example 2

Synthesis of cis-[((2,4,6-trimethylphenylamino)(pyrrolidin-1-yl)methylidene)] PdCl2 (2,4,6-trimethylphenylisonitrile) (3)

To a solution of cis-{(2,4,6-(CH3)3C6H2)NC}2PdCl2 (Id) (0.192 g, 0.411 mmol) in THF (ca. 10 mL) at 0° C., pyrrolidine (6.0292 g, 0.411 mmol) was added and the reaction mixture was stirred overnight at room temperature. The solvent was removed under reduced pressure and the residue so obtained was purified by column chromatography using silica gel as a stationary phase and by eluting with a CHCl3/CH3OH mixture (95:5 v/v) to give product (3) as a yellow solid (0.146 g, 64%).

Formula (Ib)

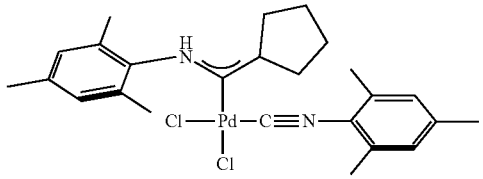

(3)

Yield: 64%
Spectral Data:
$^1$H NMR, (DMSO-d6, 400 MHz, 25° C.): δ 8.93 (s, 1H, NH), 7.09 (s, 2H, 2,4,6-(CH3)3C6H2), 7.01 (s, 1H, 2,4,6-(CH3)3C6H2), 6.79 (s, 1H, 2,4,6-(CH3)3C6H2), 4.30-4.28 (m, 2H, NC4H8), 4.15-4.11 (m, 2H, NC4H8), 2.39 (s, 3H, 2,4,6-(CH3)3C6H2), 2.28 (s, 3H, 2,4,6-(CH3)3C6H2), 2.25 (s, 3H, 2,4,6-(CH3)3C6H2), 2.20 (s, 6H, 2,4,6-(CH3)3C6H2), 2.10-1.95 (m, 4H, NC4H8), 1.93 (s, 3H, 2,4,6-(CH3)3C6H2).
$^{13}$C NMR (DMSO-d6, 100 MHz, 25° C.): δ 178.9 (NHCN), 140.8 (2,4,6-(CH3)3C6H2), 137.3 (2,4,6-(CH3)3C6H2), 137.2 (2,4,6-(CH3)3C6H2), 137.0 (2,4,6-(CH3)3C6H2), 135.4 (2,4,6-(CH3)3C6H2), 135.3 (2,4,6-(CH3)3C6H2), 135.2 (2,4,6-(CH3)3C6H2), 135.0 (2,4,6-(CH3)3C6H2), 134.1 (2,4,6-(CH3)3C6H2), 129.4 (2,4,6-(CH3)3C6H2), 129.1 (2,4,6-(CH3)3C6H2), 128.4 (2,4,6-(CH3)3C6H2), 122.1 (CN-2,4,6-(CH3)3C6H2), 55.7 (NC4H8), 49.1 (NC4H8), 25.1 (NC4H8), 24.6 (NC4H8), 20.9 (2,4,6-(CH3)3C6H2), 20.7 (2,4,6-(CH3)3C6H2), 19.6 (2,4,6-(CH3)3C6H2), 18.1 (2,4,6-(CH3)3C6H2), 17.8 {2(2,4,6-(CH3)3C6H2)}. IR data (KBr pellet): 3181 (s), 2919 (s), 2197 (s), 1556 (s), 1453 (w), 1034 (w) 856 (w) cm-1. HRMS Calcd. for [C24H31N3Cl2Pd—Cl]+ 502.1241, found m/z 502.1245. Anal. Calcd. for C24H31Cl2N3Pd: C, 53.50, H, 5.80, N, 7.80%. Found: C, 53.29, H, 5.60, N, 7.62%.

Example 3

Synthesis of cis-[((2,4,6-trimethylphenylamino)(morpholino)methylidene)]PdCl2(2,4,6-trimethylphenylisonitrile) (4)

To a solution of cis-{(2,4,6-(CH3)3C6H2)NC}2PdCl2 (Id) (0.349 g, 0.746 mmol) in THF (ca. 10 mL) at 0° C., morpholine (0.065 g, 0.747 mmol) was added and the reaction mixture was stirred overnight at room temperature. The solvent was then removed under reduced pressure and the residue so obtained was purified by column chromatography using silica gel as a stationary phase and by eluting with a CHCl3/CH3OH mixture (95:5 v/v) to give the product (4) as an yellow solid (0.253 g, 61%).

Formula (Ic)

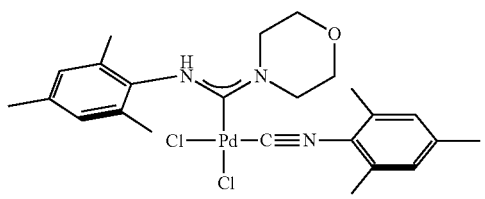

(4)

Yield: 61%
Spectral Data:
1H NMR, (DMSO-d6, 400 MHz, 25° C.): δ 9.30 (s, 1H, NH), 7.09 (s, 2H, 2,4,6-(CH3)3C6H2), 7.02 (s, 1H, 2,4,6-(CH3)3C6H2), 6.77 (s, 1H, 2,4,6-(CH3)3C6H2), 4.46-4.42 (m, 2H, NC4H8O), 3.93-3.86 (m, 2H, NC4H8O), 3.80-3.74 (m, 4H, NC4H8O), 2.39 (s, 3H, 2,4,6-(CH3)3C6H2), 2.28 (s, 3H, 2,4,6-(CH3)3C6H2), 2.25 (s, 3H, 2,4,6-(CH3)3C6H2), 2.21 (s, 6H, 2,4,6-(CH3)3C6H2), 1.92 (s, 3H, 2,4,6-(CH3)3C6H2). 13C{1H} NMR (DMSO-d6, 100 MHz, 25° C.): δ 181.8 (NHCN), 140.6 (2,4,6-(CH3)3C6H2), 137.2 (2,4,6-(CH3)3C6H2), 137.1 (2,4,6-(CH3)3C6H2), 135.2 (2,4,6-(CH3)3C6H2), 135.1 (2,4,6-(CH3)3C6H2), 134.8 {2(2,4,6-(CH3)3C6H2)}, 134.6 (2,4,6-(CH3)3C6H2), 129.4 (2,4,6-(CH3)3C6H2), 128.9 {2(2,4,6-(CH3)3C6H2)}, 128.4 (2,4,6-(CH3)3C6H2), 122.5 (CN-2,4,6-(CH3)3C6H2), 66.6 (NC4H8O), 65.7 (NC4H8O), 55.3 (NC4H8O), 47.2 (NC4H8O), 20.8 (2,4,6-(CH3)3C6H2), 20.6 (2,4,6-(CH3)3C6H2), 19.4 (2,4,6-(CH3)3C6H2), 18.0 (2,4,6-(CH3)3C6H2), 17.8 {2(2,4,6-(CH3)3C6H2)}. IR data (KBr pellet): 3196 (s), 2921 (s), 2203 (s), 1605 (w), 1555 (s), 1439 (w), 1275 (w), 1237 (w), 1115 (w), 1027 (w) 853 (w) cm-1. HRMS Calcd. for [C24H31 Cl2N3OPd—Cl]+520.1184, found m/z 520.1184. Anal. Calcd. for C24H31 Cl2N3OPd: C, 51.95, H, 5.63, N, 7.57%. Found: C, 52.34, H, 5.59, N, 7.82%.

Example 4

General Procedures for Triethoxysilylalkyne Preparation:
A mixture of terminal alkyne and EtMgBr (2.0 M in THF). in Et2O (ca. 30 mL), was added in 1.2:1 ratio at room temperature and refluxed for 2 hours. The reaction mixture was cooled to room temperature and Si(OEt)4 (1.8 times of EtMgBr) was added. The reaction mixture was again refluxed further for 12 hours. The resulting mixture was filtered, and the volatiles were removed under reduced pressure. The crude product was then purified by fractional distillation under reduced pressure at ambient temperature by Kugelrohr short path distillation apparatus at the temperature range of 40° C.-60° C.

Triethoxy(phenylethynyl)silane (6)[93]

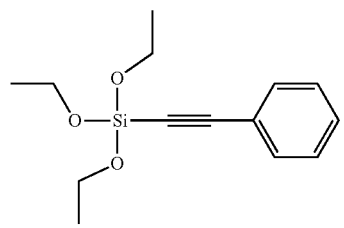

(6)

Phenyl acetylene (2.38 g, 23.3 mmol), EtMgBr (2.0 M in THF, 9.7 mL, 19.4 mmol), Si(OEt)4 (7.8 mL, 34.9 mmol). Yellow liquid; Yield (1.073 g, 21%). 1H NMR (CDCl3, 400 MHz, 25° C.): δ 7.52-7.48 (m, 2H, C6H5), 7.36-7.30 (m, 3H, C6H5), 3.85 (q, 6H, $^3J_{HH}$=7 Hz, Si(OCH2CH3)3), 1.24 (t, 9H, 3JHH=7 Hz, Si(OCH2CH3)3). 13C{1H} NMR (CDCl3, 100 MHz, 25° C.): δ 132.3 (C6H5), 129.3 (C6H5), 128.3 (C6H5), 121.9 (C6H5), 104.1 (CSi(OCH2CH3)3), 85.1 (C6H5C), 59.1 (Si(OCH2CH3)3), 18.1 (Si(OCH2CH3)3). GC-MS (ESI): =264 [M]+.

Triethoxy(p-tolylethynyl)silane (7)

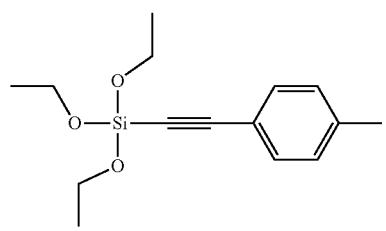

(7)

1-ethynyl-4-methylbenzene (1.022 g, 8.79 mmol), EtMgBr (2.0 M in THF, 3.7 mL, 7.33 mmol), Si(OEt)4 (2.9 mL, 13.2 mmol). Yellow liquid; Yield (0.409 g, 20%). 1H NMR (CDCl3, 400 MHz, 25° C.): δ 7.41 (d, 2H, 3JHH=8 Hz, 4-CH3C6H4), 7.12 (d, 2H, 3JHH=8 Hz, 4-CH3C6H4), 3.94 (q, 6H, 3JHH=7 Hz, Si(OCH2CH3)3), 2.35 (s, 3H, 4-CH3C6H4), 1.29 (t, 9H, 3JHH=7 Hz, Si(OCH2CH3)3). 13C{1H} NMR (CDCl3, 100 MHz, 25° C.): δ 139.7 (4-CH3C6H4), 132.4 (4-CH3C6H4), 129.2 (4-CH3C6H4), 119.0 (4-CH3C6H4), 104.6 (CSi(OCH2CH3)3), 84.4 (C6H5C), 59.2 (Si(OCH2CH3)3), 21.7 (4-CH3C6H4), 18.2 (Si(OCH2CH3)3). GC-MS (ESI): =278 [M]+.

Triethoxy(hex-1-yn-1-yl)silane (8)[93]

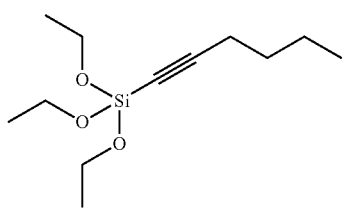
(8)

Hex-1-yne (2.25 g, 27.3 mmol), EtMgBr (2.0 M in THF, 11.4 mL, 22.8 mmol), Si(OEt)4 (9.2 mL, 41.01 mmol). Yellow liquid; Yield (1.83 g, 33%). 1H NMR (CDCl3, 400 MHz, 25° C.): δ 3.84 (q, 6H, 3JHH=7 Hz, Si(OCH2CH3)3), 2.23 (t, 2H, 3JHH=7 Hz, CH3CH2CH2CH2), 1.51 (quint, 2H, 3JHH=7 Hz, CH3CH2CH2CH2), 1.41 (quint, 2H, 3JHH=7 Hz, CH3CH2CH2CH2), 1.22 (t, 9H, 3JHH=7 Hz, Si(OCH2CH3)3), 0.88 (t, 3H, 3JHH=7 Hz, CH3CH2CH2CH2). 13C{1H}NMR (CDCl3, 100 MHz, 25° C.): δ 107.5 (CSi(OCH2CH3)3), 75.9 (C6H5C), 58.9 (Si(OCH2CH3)3), 30.3 (CH3 CH2CH2CH2), 21.9 (CH3 CH2CH2CH2), 19.3 (CH3CH2CH2CH2), 18.1 (Si(OCH2CH3)3), 13.6 (CH3CH2CH2CH2). GC-MS (ESI): = 244 [M]+.

Triethoxy(hept-1-yn-1-yl)silane (9)

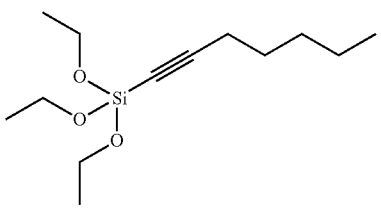
(9)

Hept-1-yne (1.00 g, 10.4 mmol), EtMgBr (2.0 M in THF, 4.3 mL, 8.66 mmol), Si(OEt)4 (3.5 mL, 15.6 mmol). Yellow liquid; Yield (0.624 g, 28%). 1H NMR (CDCl3, 500 MHz, 25° C.): δ 3.88 (q, 6H, 3JHH=7 Hz, Si(OCH2CH3)3), 2.24 (t, 2H, 3JHH=7 Hz, CH3CH2CH2CH2CH2), 1.53 (quint, 2H, 3JHH=7 Hz, CH3CH2CH2CH2CH2), 1.38-1.30 (m, 4H, CH3CH2CH2CH2CH2), 1.27-1.23 (m, 9H, Si(OCH2CH3)3), 0.89 (t, 3H, 3JHH=7 Hz, CH3CH2CH2CH2CH2). 13C{1H} NMR (CDCl3, 100 MHz, 25° C.): δ 107.5 (CSi(OCH2CH3)3), 75.9 (C6H5C), 58.9 (Si(OCH2CH3)3), 31.0 (CH3CH2CH2CH2CH2), 27.9 (CH3CH2CH2CH2CH2), 22.2 (CH3CH2CH2CH2CH2), 19.6 (CH3CH2CH2CH2CH2), 18.1 (Si(OCH2CH3)3), 14.0 (CH3CH2CH2CH2CH2). GC-MS (ESI): =243 [M-CH3]+.

Triethoxy((4-fluorophenyl)ethynyl)silane (10)

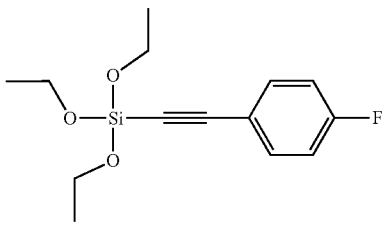
(10)

1-ethynyl-4-fluorobenzene (1.00 g, 8.32 mmol), EtMgBr (2.0 M in THF, 3.5 mL, 6.93 mmol), Si(OEt)4 (2.8 mL, 12.5 mmol). Yellow liquid; Yield (0.507 g, 26%). 1H NMR (CDCl3, 400 MHz, 25° C.): δ 7.51-7.46 (m, 2H, 4-FC6H4), 7.02-6.97 (m, 2H, 4-FC6H4), 3.92 (q, 6H, 3JHH=7 Hz, Si(OCH2CH3)3), 1.31 (t, 9H, 3JHH=7 Hz, Si(OCH2CH3)3). 13C{1H}NMR(CDCl3, 100 MHz, 25° C.): δ 162.9 (d, 1JCF=248 Hz, 4-FC6H4), 134.2 (4-FC6H4), 134.1 (4-FC6H4), 118.4 (C6H5C), 115.8 (d, 2JCF=22 Hz, 4-FC6H4), 82.7 (CSi(OCH2CH3)3), 59.2 (Si(OCH2CH3)3), 18.2 (Si(OCH2CH3)3). GC-MS (ESI): =282 [M]+.

((4-Chlorophenyl)ethynyl)triethoxysilane (11)

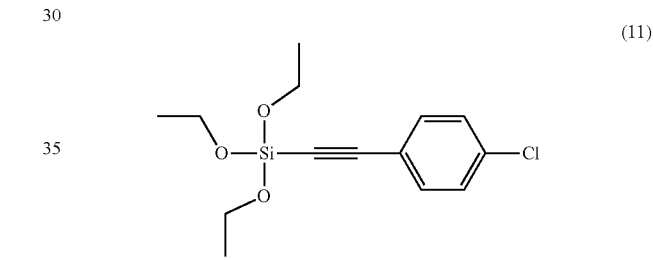
(11)

1-chloro-4-ethynylbenzene (1.00 g, 7.32 mmol), EtMgBr (2.0 M in THF, 3.1 mL, 6.10 mmol), Si(OEt)4 (2.5 mL, 10.98 mmol). Yellow liquid; Yield (0.602 g, 33%). 1H NMR (CDCl3, 500 MHz, 25° C.): δ 7.51-7.42 (m, 2H, 4-ClC6H4), 7.33-7.28 (m, 2H, 4-ClC6H4), 3.87 (q, 6H, 3JHH=8 Hz, Si(OCH2CH3)3), 1.26 (t, 9H, 3JHH=8 Hz, Si(OCH2CH3)3). 13C{1H} NMR (CDCl3, 125 MHz, 25° C.): δ 135.1 (4-ClC6H4), 133.5 (4-ClC6H4), 128.8 (4-ClC6H4), 121.3 (4-ClC6H4), 105.6 (CSi(OCH2CH3)3), 90.0 (C6H5C), 59.3 (Si(OCH2CH3)3), 18.2 (Si(OCH2CH3)3). GC-MS (ESI): = 298 [M]+.

((4-Bromophenyl)ethynyl)triethoxysilane (12)

(12)

1-bromo-4-ethynylbenzene (1.00 g, 5.52 mmol), EtMgBr (2.0 M in THF, 2.3 mL, 4.60 mmol), Si(OEt)4 (1.9 mL, 8.28 mmol). Yellow liquid; Yield (0.436 g, 27%). 1H NMR (CDCl3, 500 MHz, 25° C.): δ 7.45 (d, 2H, 3JHH=8 Hz 4-BrC6H4), 7.34 (d, 2H, 3JHH=8 Hz, 4-BrC6H4), 3.85 (q, 6H, 3JHH=7 Hz, Si(OCH2CH3)3), 1.24 (t, 9H, 3JHH=7 Hz, Si(OCH2CH3)3). 13C{1H} NMR (CDCl3, 125 MHz, 25° C.): δ 133.7 (4-BrC6H4), 131.7 (4-BrC6H4), 128.5 (4-BrC6H4), 123.3 (4-BrC6H4), 105.9 (CSi(OCH2CH3)3), 90.7 (C6H5C), 59.3 (Si(OCH2CH3)3), 18.2 (Si(OCH2CH3)3). GC-MS (ESI): =343 [M]+.

Example 5

Triethoxy(naphthalen-1-ylethynyl)silane (13)

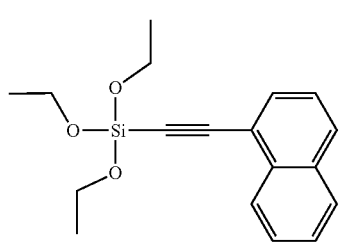

A mixture of 1-ethynylnaphthalene (1.00 g, 6.57 mmol) and EtMgBr (2.0 M in THF, 16.4 mL, 32.9 mmol), in Et2O (ca. 30 mL), was added at room temperature and refluxed for 2 hours. The reaction mixture was cooled to room temperature and Si(OEt)4 (2.6 mL, 11.8 mmol) was added. The reaction mixture again refluxed further for 12 hours. The resulting mixture was filtered, and the volatiles were removed under reduced pressure. The crude product was then purified by fractional distillation under reduced pressure at ambient temperature by Kugelrohr short path distillation apparatus at the temperature range of 40° C.-60° C.

Yellow liquid; Yield (0.283 g, 14%). 1H NMR (CDCl3, 400 MHz, 25° C.): δ 8.36 (d, 1H, 3JHH=8 Hz C10H7), 7.85 (d, 2H, 3JHH=8 Hz, C10H7), 7.74 (d, 1H, 3JHH=7 Hz, C10H7), 7.59 (t, 1H, 3JHH=7 Hz, C10H7), 7.52 (t, 1H, 3JHH=7 Hz, C10H7), 7.42 (t, 1H, 3JHH=7 Hz, C10H7), 3.85 (q, 6H, 3JHH=7 Hz, Si(OCH2CH3)3), 1.24 (t, 9H, 3JHH=7 Hz, Si(OCH2CH3)3). 13C{1H} NMR (CDCl3, 100 MHz, 25° C.): δ 133.7 (C10H7), 133.2 (C10H7), 131.4 (C10H7), 129.5 (C10H7), 128.4 (C10H7), 127.1 (C10H7), 126.6 (C10H7), 126.4 (C10H7), 125.2 (C10H7), 120.6 (C10H7), 104.9 (CSi(OCH2CH3)3), 94.4 (C6H5C), 59.3 (Si(OCH2CH3)3), 18.3 (Si(OCH2CH3)3). GC-MS (ESI): =314 [M]+.

Example 6

General Procedure for the C—C Coupling Reaction of the Csp2-Csp Type Hiyama Alkynylation Reaction In a typical catalysis run, performed in air, a 25 mL round bottom flask charged with a mixture of iodobenzene, triethoxysilylalkyne, and NaOH, in the molar ratio of 1:1.2:3. Palladium complex 4 (2 mol %) was added to the mixture followed by 6 mL solvent (dioxane/H2O, 4:2 v/v) and the reaction mixture was heated at 80° C. for 4 hours. The reaction mixture was cooled to room temperature and water (ca. 12 mL) was added. The resultant mixture was extracted with EtOAc (ca. 50 mL). The aqueous layer was further extracted with EtOAc (ca. 3×20 mL). The organic layers were combined and vacuum dried to obtain a crude product that was subsequently purified by column chromatography using silica gel as a stationary phase and eluting it with mixed medium of petroleum ether/EtOAc to give the desired product.

Equation 1.
Hiyama coupling reaction of iodobenzene (5) with triethoxysilylalkynes (6-13) as catalyzed by Pd—ADC complex (4).

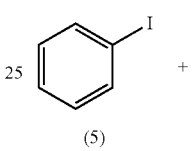

(5)

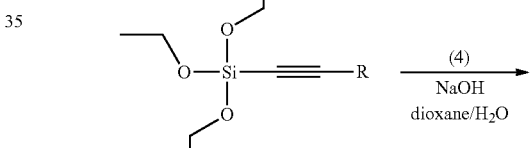

R = C6H5 (6)
R = 4-CH3C6H4 (7)
R = CH3(CH2)2CH2 (8)
R = CH3(CH2)3CH2 (9)
R = 4-FC6H5 (10)
R = 4-ClC6H4 (11)
R = 4-BrC6H4 (12)
R = C10H7 (13)

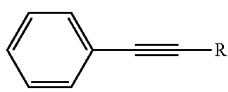

R = C6H5 (14)
R = 4-CH3C6H4 (15)
R = CH3(CH2)2CH2 (16)
R = CH3(CH2)3CH2 (17)
R = 4-FC6H5 (18)
R = 4-ClC6H4 (19)
R = 4-BrC6H4 (20)
R = C10H7 (21)

TABLE 1

Selected results for Hiyama cross-coupling reaction of iodobenzene with triethoxysilylalkynes as catalyzed by Pd-ADC complex 4.

| S.No. | iodobenzene | triethoxysilylalkyne | cross-coupled product | time (hours) | yield (%)[a] |
|---|---|---|---|---|---|
| 1 | (5) | (6) | (14) | 4 | 76 |
| 2 | (5) | (7) | (15) | 4 | 68 |
| 3 | (5) | (8) | (16) | 4 | 41 |
| 4 | (5) | (9) | (17) | 4 | 35 |
| 5 | (5) | (10) | (18) | 4 | 68 |

TABLE 1-continued

Selected results for Hiyama cross-coupling reaction of iodobenzene with triethoxysilylalkynes as catalyzed by Pd-ADC complex 4.

| S.No. | iodobenzene | triethoxysilylalkyne | cross-coupled product | time (hours) | yield (%)[a] |
|---|---|---|---|---|---|
| 6 | (5) | (11) | (19) | 4 | 58 |
| 7 | (5) | (12) | (20) | 4 | 48 |
| 8 | (5) | (13) | (21) | 4 | 40 |

Reaction conditions: iodobenzene (1.00 mmol), triethoxysilylalkyne (1.20 mmol), NaOH (3.00 mmol), in presence of catalyst 4 (2 mol %) and 6 mL of a mixed medium of 1,4-dioxane:H2O (4:2 v/v ratio) at 80° C. for 4 hours.
[a]isolated yields.

Scheme 3.
Proposed mechanism for the Hiyama coupling reaction between two representative iodobenzene and triethyoxy(phenylethynyl)silane substrates as catalyzed by Pd—ADC complex (4).

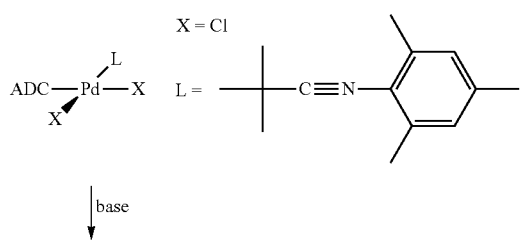

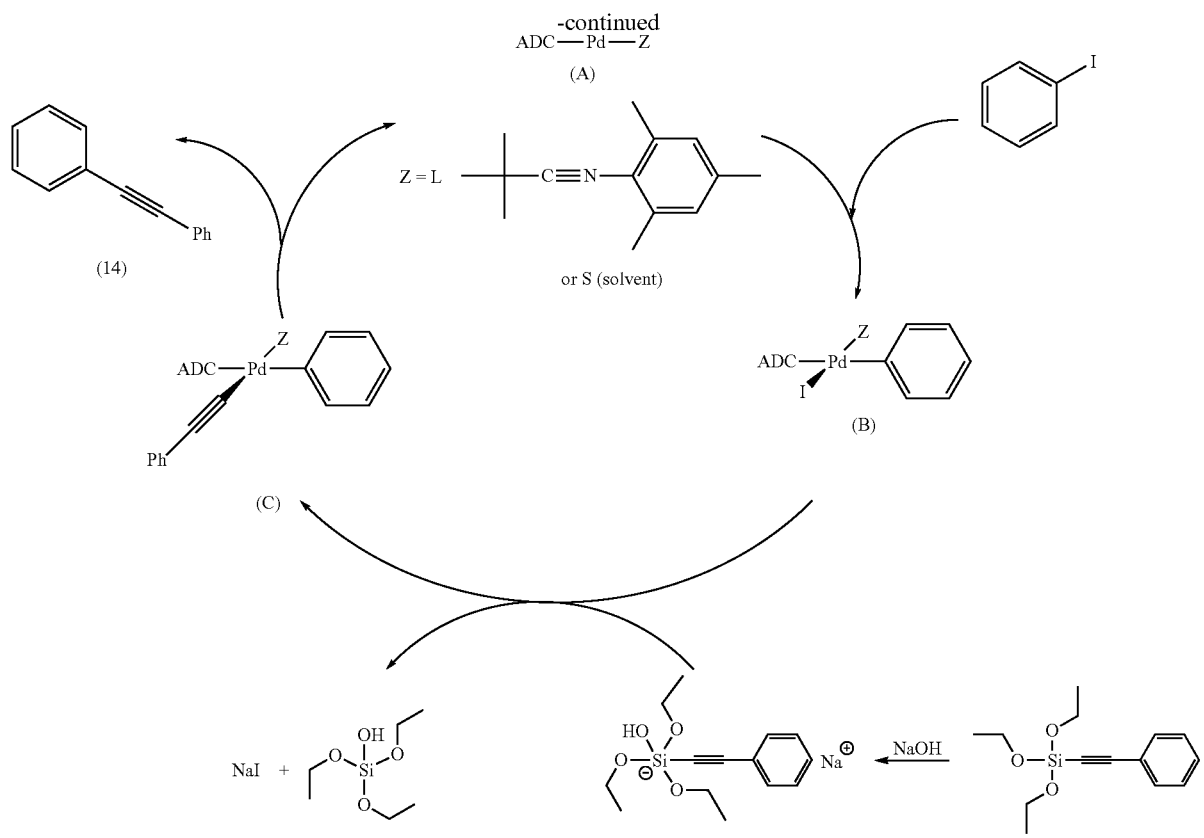

Example 7

Procedure for Mercury (Hg) Drop Test

A 25 mL round bottom flask was charged with a mixture of the iodobenzene, triethoxysilylalkyne and NaOH, in the molar ratio of 1:1.2:3. Palladium complex 4 (2 mol %) and excess Hg, were added to the mixture followed by 6 mL solvent (dioxane/H2O, 4:2 v/v) and the reaction mixture was heated at 80° C. for 4 hours. The reaction mixture was cooled to room temperature and water (ca. 12 mL) was added. The resultant mixture was extracted with EtOAc (ca. 50 mL). The aqueous layer was further extracted with EtOAc (ca. 3×20 mL). The organic layers were combined and vacuum dried to obtain a crude product that was subsequently purified by column chromatography using silica gel as a stationary phase and eluting it with mixed medium of petroleum ether/EtOAc to give the desired product.

1,2-Diphenylethyne (14)

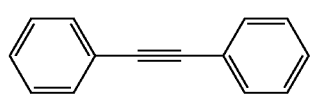

Triethoxy(phenylethynyl)silane (6) (0.317 g, 1.20 mmol), iodobenzene (0.204 g, 1.00 mmol), NaOH (0.120 g, 3.00 mmol), catalyst (4) (1.11×10-3 g, 0.02 mmol). White solid; Yield (0.136 g, 76%). 1H NMR (CDCl3, 500 MHz, 25° C.): δ 7.56-7.54 (m, 2H, C6H5), 7.38-7.34 (m, 3H, C6H5). 13C{1H} NMR (CDCl3, 125 MHz, 25° C.): δ 131.7 (C6H5), 128.5 (C6H5), 128.4 (C6H5), 123.4 (C6H5), 89.5 (C6H5C). Anal. Calcd. for C14H10: C, 94.34, H, 5.66%. Found: C, 94.57, H, 5.43%. GC-MS (ESI): =178 [M]+.

1-Methyl-4-(phenylethynyl)benzene (15)

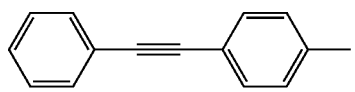

Triethoxy(p-tolylethynyl)silane (7) (0.333 g, 1.20 mmol), iodobenzene (0.204 g, 1.00 mmol), NaOH (0.120 g, 3.00 mmol), catalyst (4) (1.11×10-3 g, 0.02 mmol). White solid; Yield (0.131 g, 68%). 1H NMR (CDCl3, 500 MHz, 25° C.): δ 7.53 (d, 2H, 3JHH=8 Hz, C6H5), 7.44 (d, 2H, 3JHH=8 Hz, 4-CH3C6H4), 7.37-7.33 (m, 3H, C6H5), 7.17 (d, 2H, 3JHH=8 Hz, 4-CH3C6H4), 2.38 (s, 3H, 4-CH3C6H4). 13C{1H} NMR (CDCl3, 125 MHz, 25° C.): δ 138.5 (4-CH3C6H4), 131.7 (4-CH3C6H4), 131.6 (C6H5), 129.3 (C6H5), 128.5 (C6H5), 128.2 (C6H5), 123.6 (4-CH3C6H4), 120.3 (4-CH3C6H4), 89.7 (4-CH3C6H4C), 88.8 (C6H5C), 21.6 (4-CH3C6H4). Anal. Calcd. for C15H12: C, 93.71, H, 6.29%. Found: C, 93.61, H, 6.33%. GC-MS (ESI): =192 [M]+.

Hex-1-yn-1-ylbenzene (16)

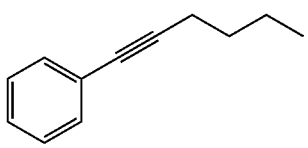

Triethoxy(hex-1-yn-1-yl)silane (8) (0.293 g, 1.20 mmol), iodobenzene (0.204 g, 1.00 mmol), NaOH (0.120 g, 3.00 mmol), catalyst (4) (1.11×10-3 g, 0.02 mmol). Colorless oil; Yield (0.064 g, 41%). 1H NMR (CDCl3, 500 MHz, 25° C.): δ 7.40-7.38 (m, 2H, C6H5), 7.28-7.26 (m, 3H, C6H5), 2.41 (t, 2H, 3JHH=7 Hz, CH3CH2CH2CH2), 1.60 (quint, 2H, 3JHH=7 Hz, CH3CH2CH2CH2), 1.47 (quint, 2H, 3JHH=7 Hz, CH3CH2CH2CH2), 0.95 (t, 3H, 3JHH=7, Hz, CH3CH2CH2CH2). 13C{1H} NMR (CDCl3, 125 MHz, 25° C.): δ 131.7 (C6H5), 128.3 (C6H5), 127.6 (C6H5), 124.2 (C6H5), 90.5 (C6H5C), 80.6 (CH3CH2CH2CH2C), 31.0 (CH3 CH2CH2CH2), 22.2 (CH3 CH2CH2CH2), 19.2 (CH3CH2CH2CH2), 13.8 (CH3CH2CH2CH2). Anal. Calcd. for C12H14: C, 91.08, H, 8.92%. Found: C, 91.15, H, 8.60, %. GC-MS (ESI): =158 [M]+.

Hept-1-yn-1-ylbenzene (17)

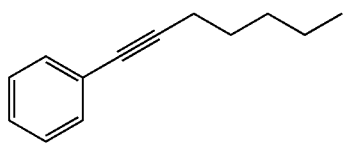

Triethoxy(hept-1-yn-1-yl)silane (9) (0.3101 g, 1.20 mmol), iodobenzene (0.204 g, 1.00 mmol), NaOH (0.120 g, 3.00 mmol), catalyst (4) (1.11×10-3 g, 0.02 mmol). Colorless oil; Yield (0.061 g, 35%). 1H NMR (CDCl3, 500 MHz, 25° C.): δ 7.40-7.39 (m, 2H, C6H5), 7.28-7.26 (m, 3H, C6H5), 2.41 (t, 2H, 3JHH=7 Hz, CH3CH2CH2CH2CH2), 1.62 (quint, 2H, 3JHH=7 Hz, CH3CH2CH2CH2CH2), 1.44 (quint, 2H, 3JHH=7 Hz, CH3CH2CH2CH2CH2), 1.37 (quint, 2H, 3JHH=7 Hz, CH3CH2CH2CH2CH2), 0.93 (t, 3H, 3JHH=7 Hz, CH3CH2CH2CH2CH2). 13C{1H} NMR (CDCl3, 125 MHz, 25° C.): δ 131.7 (C6H5), 128.3 (C6H5), 127.6 (C6H5), 124.3 (C6H5), 90.6 (C6H5C), 80.7 (CH3CH2CH2CH2CH2C), 31.3 (CH3CH2CH2CH2CH2), 28.6 (CH3CH2CH2CH2CH2), 22.4 (CH3CH2CH2CH2CH2), 19.5 (CH3CH2CH2CH2CH2), 14.1 (CH3CH2CH2CH2CH2). Anal. Calcd. for C13H16: C, 90.64, H, 9.36%. Found: C, 90.59, H, 9.48%. GC-MS (ESI): =172 [M]+.

1-Fluoro-4-(phenylethynyl)benzene (18)

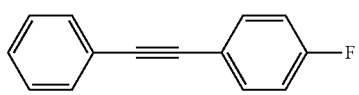

Triethoxy((4-fluorophenyl)ethynyl)silane (10) (0.338 g, 1.20 mmol), iodobenzene (0.204 g, 1.00 mmol), NaOH (0.120 g, 3.00 mmol), catalyst (4) (1.11×10-3 g, 0.02 mmol). White solid; Yield (0.133 g, 68%). 1H NMR (CDCl3, 500 MHz, 25° C.): δ 7.53-7.50 (m, 4H, 4-FC6H4), 7.37-7.33 (m, 3H, C6H5), 7.05 (t, 2H, 3JHH=8 Hz, C6H5). 13C{1H} NMR CDCl3, 125 MHz, 25° C.): δ 162.6 (d, 1JCF=247 Hz, 4-FC6H4), 133.6 (d, 3JCF=8.75 Hz, 4-FC6H4), 131.7 (C6H5), 128.5 (C6H5), 128.4 (C6H5), 123.2 (C6H5), 119.5 (4-FC6H4), 115.9 (d, 2JCF=22 Hz, 4-FC6H4), 89.2 (4-FC6H4C), 88.4 (C6H5C). Anal. Calcd. for C14H9F: C, 85.69, H, 4.62%. Found: C, 85.52, H, 4.32%. GC-MS (ESI): =196 [M]+.

1-Chloro-4-(phenylethynyl)benzene (19)

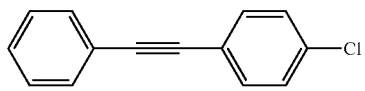

((4-chlorophenyl)ethynyl)triethoxysilane (11) (0.358 g, 1.20 mmol), iodobenzene (0.204 g, 1.00 mmol), NaOH (0.120 g, 3.00 mmol), catalyst (4) (1.11×10-3 g, 0.02 mmol). White solid; Yield (0.103 g, 48%). 1H NMR (CDCl3, 400 MHz, 25° C.): δ 7.54-7.52 (m, 2H, 4-ClC6H4), 7.46 (d, 2H, 3JHH=8 Hz, 4-ClC6H4), 7.36-7.34 (m, 4H, C6H5), 7.32 (br, 1H, C6H5). $^{13}$C{1H} NMR (CDCl3, 100 MHz, 25° C.): δ 134.4 (4-ClC6H4), 132.9 (C6H5), 131.7 (C6H5), 128.8 (C6H5), 128.6 (4-ClC6H4), 128.5 (C6H5), 123.0 (4-ClC6H4), 121.9 (4-ClC6H4), 90.4 (4-ClC6H4C), 88.4 (C6H5C). Anal. Calcd. for C14H9Cl: C, 79.07, H, 4.27%. Found: C, 78.80, H, 4.56%. GC-MS (ESI): =212 [M]+.

1-Bromo-4-(phenylethynyl)benzene (20)

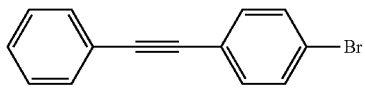

((4-bromophenyl)ethynyl)triethoxysilane (12) (0.412 g, 1.20 mmol), iodobenzene (0.204 g, 1.00 mmol), NaOH (0.120 g, 3.00 mmol), catalyst (4) (1.11×10-3 g, 0.02 mmol). White solid; Yield (0.149 g, 58%). 1H NMR (CDCl3, 500 MHz, 25° C.): δ 7.54-7.52 (m, 2H, 4-BrC6H4), 7.48 (d, 2H, 3JHH=8 Hz, 4-BrC6H4), 7.39 (d, 2H, 3JHH=8 Hz, C6H5), 7.36-7.34 (m, 3H, C6H5). 13C{1H} NMR (CDCl3, 125 MHz, 25° C.): δ 133.1 (4-BrC6H4), 131.7 (4-BrC6H4), 131.7 (4-BrC6H4), 128.6 (C6H5), 128.5 (4-BrC6H4), 123.0 (C6H5), 122.6 (C6H5), 122.3 (4-BrC6H4), 90.6 (4-BrC6H4C), 88.4 (C6H5C). Anal. Calcd. for C14H9Br: C, 65.40, H, 3.53%. Found: C, 65.18, H, 3.56%. GC-MS (ESI): =257 [M]+.

1-(Phenylethynyl)naphthalene (21)

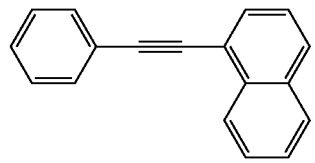

(21)

Triethoxy(naphthalen-1-ylethynyl)silane (13) (0.377 g, 1.20 mmol), iodobenzene (0.204 g, 1.00 mmol), NaOH (0.120 g, 3.00 mmol), catalyst (4) (1.11×10-3 g, 0.02 mmol). Colorless oil; Yield (0.092 g, 40%). 1H NMR (CDCl3, 500 MHz, 25° C.): δ 8.47 (d, 1H, 3JHH=8 Hz C10H7) 7.88 (d, 1H, 3JHH=8 Hz, C10H7), 7.86 (d, 1H, 3JHH=8 Hz, C10H7), 7.79 (d, 1H, 3JHH=7 Hz, C10H7), 7.67 (d, 2H, 3JHH=8 Hz, C6H5), 7.62 (t, 1H, 3JHH=8 Hz, C10H7), 7.56 (t, 1H, 3JHH=8 Hz, C10H7), 7.49 (t, 1H, 3JHH=8 Hz, C10H7), 7.47-7.43 (m, 3H, C6H5). 13C{1H} NMR (CDCl3, 125 MHz, 25° C.): δ 133.4 (C6H5), 133.3 (C6H5), 131.8 {2(C10H7)}, 130.5 (C10H7), 128.9 (C10H7), 128.6 {2(C10H7)}, 128.5 (C6H5), 128.4 (C10H7), 126.9 (C10H7), 126.6 (C10H7), 126.4 (C10H7), 125.4 (C6H5), 123.5 (C6H5), 121.0 (C6H5), 94.4 (C10H7C), 86.7 (C6H5C). Anal. Calcd. for C18H12: C, 94.70, H, 5.30%. Found: C, 94.92, H, 4.96%. GC-MS (ESI): =228 [M]$^+$.

Example 8

General Procedure for Csp2-Csp Type C—C Coupling Reaction Followed by Cyclization in Hiyama Coupling In a typical catalysis run, performed in air, a 25 mL round bottom flask was charged with a mixture of the 2-iodophenol, a triethoxysilylalkyne, and NaOH, in the molar ratio of 1:1.2:3. Palladium complexes 4 (2 mol %) was added to the mixture followed by 6 mL solvent (dioxane/H2O, 4:2 v/v) and the reaction mixture was heated at 80° C. for 4 hours. The reaction mixture was cooled to room temperature and water (ca. 12 mL) was added. The resultant mixture was extracted with EtOAc (ca. 50 mL). The aqueous layer was further extracted with EtOAc (ca. 3×20 mL). The organic layers were combined and vacuum dried to obtain a crude product that was subsequently purified by column chromatography using silica gel as a stationary phase and eluting it with mixed medium of petroleum ether/EtOAc to give the desired product.

Equation 2.
Hiyama coupling reaction followed by cyclization of iodophenol (22) with triethoxysilylalkynes (6-13) as catalyzed by Pd—ADC complex (4).

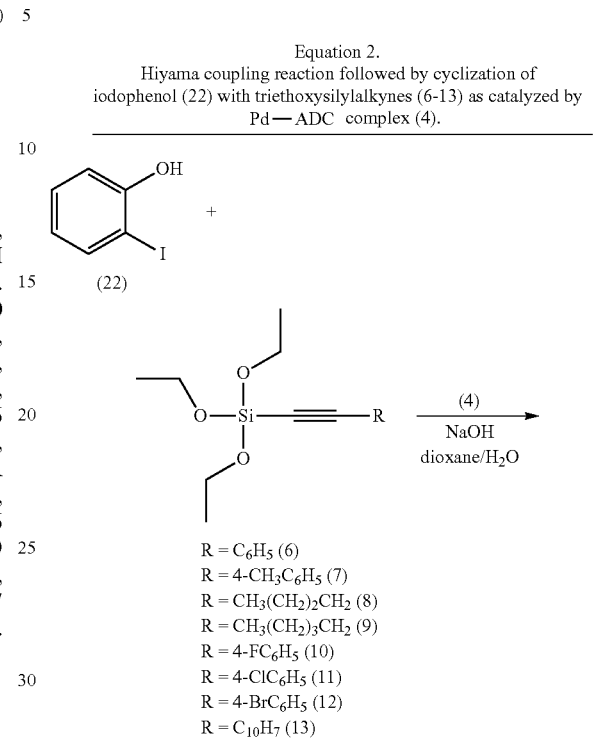

R = C6H5 (6)
R = 4-CH3C6H5 (7)
R = CH3(CH2)2CH2 (8)
R = CH3(CH2)3CH2 (9)
R = 4-FC6H5 (10)
R = 4-ClC6H5 (11)
R = 4-BrC6H5 (12)
R = C10H7 (13)

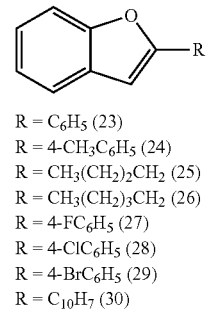

R = C6H5 (23)
R = 4-CH3C6H5 (24)
R = CH3(CH2)2CH2 (25)
R = CH3(CH2)3CH2 (26)
R = 4-FC6H5 (27)
R = 4-ClC6H5 (28)
R = 4-BrC6H5 (29)
R = C10H7 (30)

TABLE 2

Selected results for the tandem Hiyama/cyclization reaction iodophenol and various triethoxysilylalkynes as catalyzed by Pd-ADC complex 4.

| S.No | iodophenol | triethoxysilylalkyne | product | Time (hours) | Yield (%)$^a$ |
|---|---|---|---|---|---|
| 1 | (22) | (6) | (23) | 4 | 57 |

TABLE 2-continued

Selected results for the tandem Hiyama/cyclization reaction iodophenol and various triethoxysilylalkynes as catalyzed by Pd-ADC complex 4.

| S.No | iodophenol | triethoxysilylalkyne | product | Time (hours) | Yield (%)[a] |
|---|---|---|---|---|---|
| 2 | (22) | (7) | (24) | 4 | 38 |
| 3 | (22) | (8) | (25) | 4 | 24 |
| 4 | (22) | (9) | (26) | 4 | 14 |
| 5 | (22) | (10) | (27) | 24 | 39 |
| 6 | (22) | (11) | (28) | 24 | 41 |

TABLE 2-continued

Selected results for the tandem Hiyama/cyclization reaction iodophenol and various triethoxysilylalkynes as catalyzed by Pd-ADC complex 4.

| S.No | iodophenol | triethoxysilylalkyne | product | Time (hours) | Yield (%)[a] |
|---|---|---|---|---|---|
| 7 | (22) | (12) | (29) | 24 | 43 |
| 8 | (22) | (13) | (30) | 36 | 27 |

Reaction conditions: 2-iodophenol (1.00 mmol), triethoxysilylalkyne (1.20 mmol), NaOH (3.00 mmol), in presence of catalyst 4 (2 mol %) and 6 mL of a mixed medium of 1,4-dioxane:H20 (4:2 v/v ratio) at 80° C. for 4 hours.
[a]isolated yields.

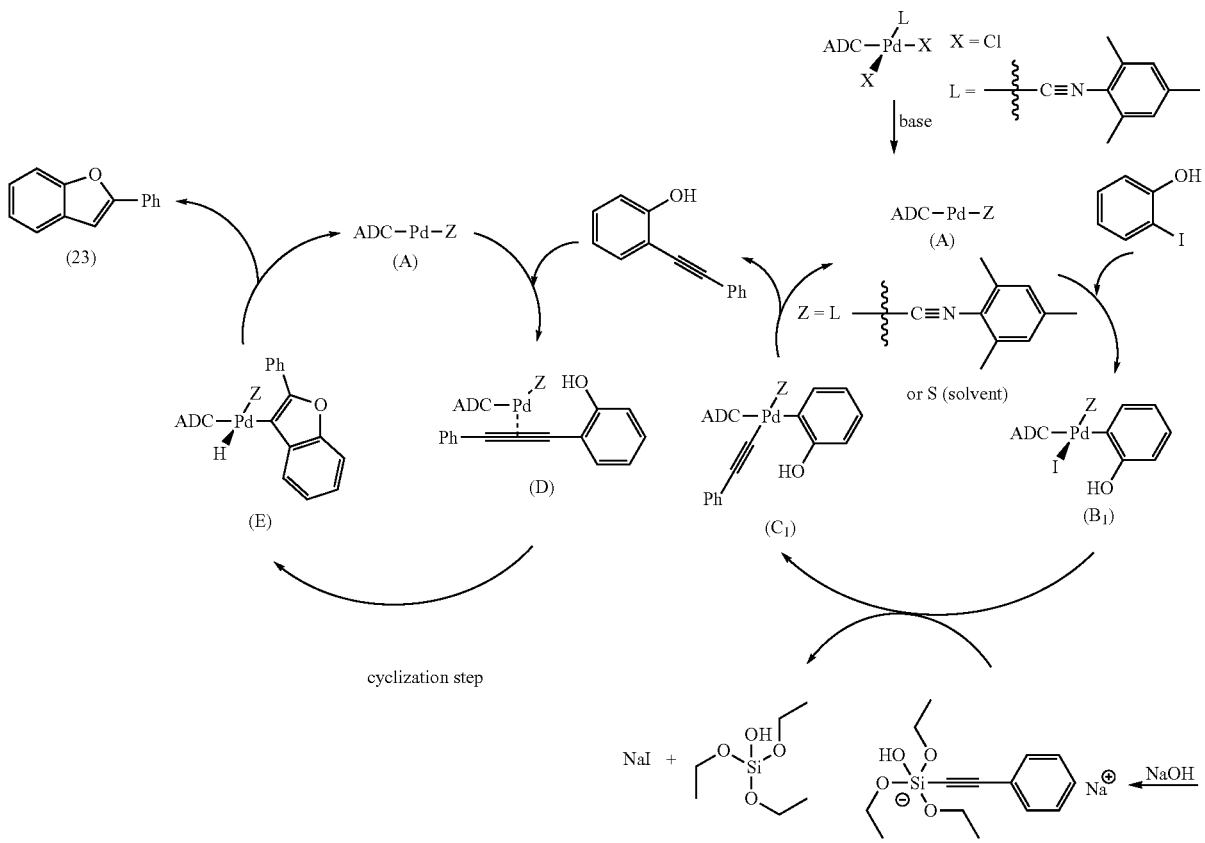

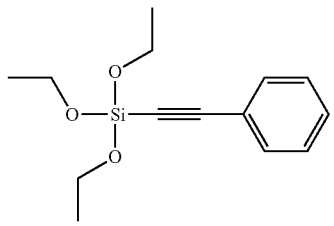

Hiyama alkynylation step

Scheme 4. Proposed mechanism for the Hiyama alkynylation/cyclization reaction between two representative 2-iodophenol and triethoxy(phenylethynyl)silane substrates as catalyzed by Pd-ADC complex (4).

Example 9

Procedure for Mercury (Hg) Drop Test

A 25 mL round bottom flask was charged with a mixture of the 2-iodophenol, a triethoxysilylalkyne and NaOH, in the molar ratio of 1:1.2:3. Palladium complexes 4 (2 mol %) and excess Hg, were added to the mixture followed by 6 mL solvent (dioxane/H2O, 4:2 v/v) and the reaction mixture was heated at 80° C. for 4 hours. The reaction mixture was cooled to room temperature and water (ca. 12 mL) was added. The resultant mixture was extracted with EtOAc (ca. 50 mL). The aqueous layer was further extracted with EtOAc (ca. 3×20 mL). The organic layers were combined and vacuum dried to obtain a crude product that was subsequently purified by column chromatography using silica gel as a stationary phase and eluting it with mixed medium of petroleum ether/EtOAc to give the desired product.

2-Phenylbenzofuran (23)

(23)

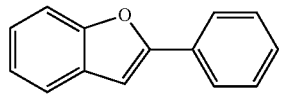

Triethoxy(phenylethynyl)silane (6) (0.317 g, 1.20 mmol), iodophenol (0.220 g, 1.00 mmol), NaOH (0.120 g, 3.00 mmol), catalyst (4) (1.11×10-3 g, 0.02 mmol). White solid; Yield (0.110 g, 57%). 1H NMR (CDCl3, 400 MHz, 25° C.): δ 7.88 (d, 2H, 3JHH=8 Hz, C6H5), 7.59 (d, 1H, 3JHH=8 Hz, C8H5O), 7.54 (d, 1H, 3JHH=8 Hz, C8H5O), 7.46 (t, 2H, 3JHH=8 Hz, C8H5O), 7.37 (t, 1H, 3JHH=8 Hz, C6H5), 7.29 (t, 1H, 3JHH=8 Hz, C6H5), 7.24 (t, 1H, 3JHH=7 Hz, C6H5), 7.04 (s, 1H, C8H5O). 13C{1H}NMR(CDCl3, 100 MHz, 25° C.): δ 156.1 (C8H5O), 155.0 (C8H5O), 130.6 (C8H5O), 129.4 (C6H5), 128.9 (C6H5), 128.7 (C8H5O), 125.1 (C6H5), 124.4 (C8H5O), 123.1 (C8H5O), 121.0 (C6H5), 111.3 (C8H5O), 101.4 (C8H5O). GC-MS (ESI): =194 [M]+. Anal. Calcd. for C14H10O: C, 86.57, H, 5.19%. Found: C, 86.71, H, 4.91%. GC-MS (ESI): =194 [M]+.

2-(p-Tolyl)benzofuran (24)

(24)

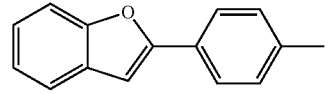

Triethoxy(p-tolylethynyl)silane (7) (0.333 g, 1.20 mmol), iodophenol (0.220 g, 1.00 mmol), NaOH (0.120 g, 3.00 mmol), catalyst (4) (1.11×10-3 g, 0.02 mmol). White solid; Yield: (0.079 g, 38%). 1H NMR (CDCl3, 500 MHz, 25° C.): δ 7.76 (d, 2H, 3JHH=8 Hz, 4-CH3C6H4), 7.58 (d, 1H, 3JHH=8 Hz, C8H5O), 7.51 (d, 1H, 3JHH=8 Hz, C8H5O), 7.27 (d, 2H, 3JHH=8 Hz, 4-CH3C6H4), 7.21 (t, 2H, 3JHH=8 Hz, C8H5O), 6.97 (s, 1H, C8H5O), 2.40 (s, 3H, 4-CH3C6H4). 13C{1H} NMR (CDCl3, 125 MHz, 25° C.): δ 156.3 (C8H5O), 154.9 (C8H5O), 138.7 (C8H5O), 129.6 (4-CH3C6H4), 129.4 (C8H5O), 127.9 (4-CH3C6H4), 125.0 (C8H5O), 124.1 (4-CH3C6H4), 123.0 (4-CH3C6H4), 120.9 (C8H5O), 111.2 (C8H5O), 100.7 (C8H5O), 21.5 (4-CH3C6H4). Anal. Calcd. for C15H12O: C, 86.51, H, 5.81%. Found: C, 86.68, H, 5.95%. GC-MS (ESI): =208 [M]+.

2-Butylbenzofuran (25)

(25)

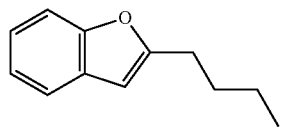

Triethoxy(hex-1-yn-1-yl)silane (8) (0.293 g, 1.20 mmol), iodophenol (0.220 g, 1.00 mmol), NaOH (0.120 g, 3.00 mmol), catalyst (4) (1.11×10-3 g, 0.02 mmol). Colorless oil; Yield: (0.041 g, 24%). 1H NMR (CDCl3, 500 MHz, 25° C.): δ 7.48 (d, 1H, 3JHH=7 Hz, C8H5O), 7.42 (d, 1H, 3JHH=9 Hz, C8H5O), 7.22-7.16 (m, 2H, C8H5O), 6.34 (s, 1H, C8H5O), 2.77 (t, 2H, 3JHH=7 Hz, CH3CH2CH2CH2), 1.75 (quint, 2H, 3JHH=7 Hz, CH3CH2CH2CH2), 1.44 (quint, 2H, 3JHH=7 Hz, CH3CH2CH2CH2), 0.96 (t, 3H, 3JHH=7 Hz, CH3CH2CH2CH2). 13C{1H} NMR (CDCl3, 125 MHz, 25° C.): δ 159.9 (C8H5O), 154.7 (C8H5O), 129.2 (C8H5O), 123.1 (C8H5O), 122.5 (C8H5O), 120.3 (C8H5O), 110.8 (C8H5O), 101.9 (C8H5O), 29.9 (CH3CH2CH2CH2), 28.3 (CH3CH2CH2CH2), 22.4 (CH3CH2CH2CH2), 13.9

(CH3CH2CH2CH2). Anal. Calcd. for C12H14O: C, 82.72, H, 8.10%. Found: C, 82.90, H, 8.44%. GC-MS (ESI): =174 [M]+.

2-Pentylbenzofuran (26)

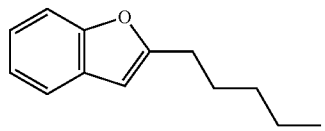
(26)

Triethoxy(hept-1-yn-1-yl)silane (9) (0.310 g, 1.20 mmol), iodophenol (0.220 g, 1.00 mmol), NaOH (0.120 g, 3.00 mmol), catalyst (4) (1.11×10-3 g, 0.02 mmol). Colorless oil; Yield: (0.026 g, 14%). 1H NMR (CDCl3, 400 MHz, 25° C.): δ 7.48 (d, 1H, 3JHH=7 Hz, C8H5O), 7.41 (d, 1H, 3JHH=7 Hz, C8H5O), 7.21-7.14 (m, 2H, C8H5O), 6.37 (s, 1H, C8H5O), 2.76 (t, 2H, 3JHH=7 Hz, CH3CH2CH2CH2CH2), 1.75 (quint, 2H, 3JHH=7 Hz, H3CH2CH2CH2CH2), 1.39-1.34 (m, 4H, CH3CH2CH2CH2CH2), 0.91 (t, 3H, 3JHH=7 z, CH3CH2CH2CH2CH2). $^{13}$C{1H}NMR (CDCl3, 125 MHz, 25° C.): δ 159.9 (C8H5O), 154.7 (C8H5O), 129.2 (C8H5O), 123.1 (C8H5O), 122.5 (C8H5O), 120.3 (C8H5O), 110.8 (C8H5O), 101.9 (C8H5O), 31.5 (CH3CH2CH2CH2CH2), 28.6 (CH3CH2CH2CH2CH2), 27.5 (CH3CH2CH2CH2CH2) 22.6 (CH3CH2CH2CH2CH2), 14.1 (CH3CH2CH2CH2CH2). Anal. Calcd. for C13H16O: C, 82.94, H, 8.57%. Found: C, 82.64, H, 8.36%. GC-MS (ESI): =188 [M]+.

2-(4-Fluorophenyl)benzofuran (27)

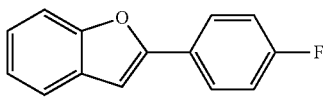
(27)

Triethoxy((4-fluorophenyl)ethynyl)silane (10) (0.338 g, 1.20 mmol), iodophenol (0.220 g, 1.00 mmol), NaOH (0.120 g, 3.00 mmol), catalyst (4) (1.11×10-3 g, 0.02 mmol). White solid; Yield: (0.083 g, 39%). 1H NMR (CDCl3, 500 MHz, 25° C.): δ 7.86-7.83 (m, 2H, 4-FC6H4), 7.58 (d, 1H, 3JHH=8 Hz, C8H5O), 7.52 (d, 1H, 3JHH=8 Hz, C8H5O), 7.28 (t, 1H, 3JHH=8 Hz, C8H5O), 7.23 (t, 1H, 3JHH=8 Hz, C8H5O), 7.14 (t, 2H, 3JHH=8 Hz, 4-FC6H4), 6.96 (s, 1H, C8H5O). 13C{1H} NMR (CDCl3, 125 MHz, 25° C.): δ 163.0 (d, 1JCF=247 Hz, 4-FC6H4), 155.1 (C8H5O), 155.0 (C8H5O), 134.7 (d, 3JCF=9 Hz, 4-FC6H4), 126.9 (4-FC6H4), 126.8 (C8H5O), 124.4 (C8H5O), 123.2 (C8H5O), 121.0 (C8H5O), 116.0 (d, 2JCF=22 Hz, 4-FC6H4), 111.3 (C8H5O), 101.2 (C8H5O). Anal. Calcd. for C14H9FO: C, 79.23, H, 4.27%. Found: C, 78.96, H, 3.90%. GC-MS (ESI): =212 [M]+.

2-(4-Chlorophenyl)benzofuran (28)

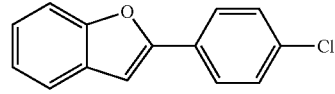
(28)

((4-chlorophenyl)ethynyl)triethoxysilane (11) (0.358 g, 1.20 mmol), iodophenol (0.220 g, 1.00 mmol), NaOH (0.120 g, 3.00 mmol), catalyst (4) (1.11×10-3 g, 0.02 mmol). White solid; Yield: (0.094 g, 41%). 1H NMR (CDCl3, 400 MHz, 25° C.): δ 7.79 (d, 2H, 3JHH=9 Hz 4-ClC6H4), 7.59 (d, 1H, 3JHH=8 Hz, C8H5O), 7.51 (d, 1H, 3JHH=8 Hz, C8H5O), 7.42 (d, 2H, 3JHH=9 Hz 4-ClC6H4), 7.30 (t, 1H, 3JHH=7 Hz, C8H5O), 7.23 (t, 1H, 3JHH=7 Hz, C8H5O), 7.01 (s, 1H, C8H5O). 13C{1H} NMR (CDCl3, 100 MHz, 25° C.): δ 155.0 (C8H5O), 154.9 (C8H5O), 134.4 (4-ClC6H4), 129.2 (C8H5O), 129.2 (4-ClC6H4), 126.3 {2(4-ClC6H4)}, 124.7 (C8H5O), 123.2 (C8H5O), 121.1 (C8H5O), 111.3 (C8H5O), 101.9 (C8H5O). Anal. Calcd. For C14H9ClO: C, 73.53, H, 3.97%. Found: C, 73.76, H, 3.63%. GC-MS (ESI): =228 [M]+.

2-(4-Bromophenyl)benzofuran (29)

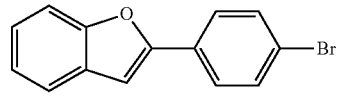
(29)

((4-bromophenyl)ethynyl)triethoxysilane (12) (0.412 g, 1.20 mmol), iodophenol (0.220 g, 1.00 mmol), NaOH (0.120 g, 3.00 mmol), catalyst (4) (1.11×10-3 g, 0.02 mmol). White solid; Yield: (0.117 g, 43%). 1H NMR (CDCl3, 500 MHz, 25° C.): δ 7.73 (d, 2H, 3JHH=7 Hz 4-BrC6H4), 7.59-7.56 (m, 3H, C8H5O & 4-BrC6H4), 7.51 (d, 1H, 3JHH=8 Hz, C8H5O), 7.30 (t, 1H, 3JHH=8 Hz, C8H5O), 7.23 (t, 1H, 3JHH=8 Hz, C8H5O), 7.03 (s, 1H, C8H5O). $^{13}$C{1H} NMR (CDCl3, 125 MHz, 25° C.): δ 155.1 (C8H5O), 154.9 (C8H5O), 132.1 (4-BrC6H4), 129.6 (C8H5O), 129.2 (4-BrC6H4), 126.5 (4-BrC6H4), 124.7 (C8H5O), 123.2 (C8H5O), 122.6 (4-BrC6H4), 121.2 (C8H5O), 111.3 (C8H5O), 102.0 (C8H5O). Anal. Calcd. for C14H9BrO: C, 61.57, H, 3.32%. Found: C, 61.77, H, 3.64%. GC-MS (ESI): =273 [M]+.

2-(Naphthalen-1-yl)benzofuran (30)

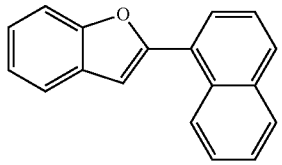
(30)

Triethoxy(naphthalen-1-ylethynyl)silane (13) (0.377 g, 1.20 mmol), iodophenol (0.220 g, 1.00 mmol), NaOH (0.120 g, 3.00 mmol), catalyst (4) (1.11×10-3 g, 0.02 mmol). White solid; Yield: (0.066 g, 27%). 1H NMR (CDCl3, 400 MHz, 25° C.): δ 8.51 (d, 1H, 3JHH=8 Hz C8H5O), 7.96-7.91 (m, 3H, C10H7), 7.70 (d, 1H, 3JHH=8 Hz, C8H5O), 7.64-7.56 (m, 4H, C10H7), 7.39-7.30 (m, 2H, C8H5O), 7.11 (s, 1H, C8H5O). 13C{1H} NMR (CDCl3, 100 MHz, 25° C.): δ 155.7 (C8H5O), 155.1 (C8H5O), 134.1 (C8H5O), 130.8 (C8H5O), 129.7 (C10H7), 129.2 (C8H5O), 128.7 (C10H7), 128.4 (C8H5O), 127.4 (C10H7), 127.0 (C10H7), 126.3 (C10H7), 125.6 (C10H7), 125.4 (C10H7), 124.5 (C10H7), 123.1 (C10H7), 121.1 (C10H7), 111.4 (C8H5O), 106.1 (C8H5O). Anal. Calcd. for C18H12O: C, 88.50, H, 4.95%. Found: C, 88.58, H, 4.54%. GC-MS (ESI): =244 [M]+.

Example 10

Synthesis of 2-Phenylbenzofuran (23) from 2-(phenylethynyl)phenol

A 25 mL round bottom flask was charged with a mixture of the 2-(phenylethynyl)phenol (0.194 g, 1.00 mmol), NaOH (0.120 g, 3.00 mmol) and catalyst 4 (1.11×10-3 g, 0.02 mmol) in the mixed medium of dioxane/H$_2$O as solvent, (ca. 6 mL, 4:2 v/v). The reaction mixture was heated at 80° C. for 4 hours. The reaction mixture was cooled to room temperature and water (ca. 12 mL) was added. The resultant mixture was extracted with EtOAc (ca. 50 mL). The aqueous layer was further extracted with EtOAc (ca. 3×20 mL). The organic layers were combined and vacuum dried to obtain a crude product that was subsequently purified by column chromatography using silica gel as a stationary phase and eluting it with mixed medium of petroleum ether/EtOAc to give the desired product as white solid; Yield (0.157 g, 81%). 1H NMR (CDCl3, 500 MHz, 25° C.): δ 7.88 (d, 2H, 3JHH=8 Hz, C6H5), 7.59 (d, 1H, 3JHH=8 Hz, C8H5O), 7.54 (d, 1H, 3JHH=8 Hz, C8H5O), 7.46 (t, 2H, 3JHH=8 Hz, C8H5O), 7.36 (t, 1H, 3JHH=7 Hz, C6H5), 7.29 (t, 1H, 3JHH=7 Hz/C6H5), 7.24 (t, 1H, 3JHH=8 Hz, C6H5), 7.04 (s, 1H, C8H5O). 13C{1H} NMR (CDCl3, 125 MHz, 25° C.): δ 156:1 (C8H5O), 155.0 (C8H5O), 130.6 (C8H5O), 129.3 (C6H5), 128.9 (C6H5), 128.7 (C8H5O), 125.1 (C6H5), 124.4 (C8H5O), 123.1 (C8H5O), 121.0 (C6H5), 111.3 (C8H5O), 101.4 (C8H5O). GC-MS (ESI): =194 [M]+.

What is claimed is:

1. An Acyclic diaminocarbene complex selected from:
(i). cis-[(2,4,6-(CH$_3$)$_3$C$_6$H$_2$NH)(NC$_5$H$_{10}$)methylidene] PdCl$_2$(CN-2,4,6-(CH$_3$)$_3$C$_6$H$_2$) having formula (Ia):

Formula (Ia)

(2)

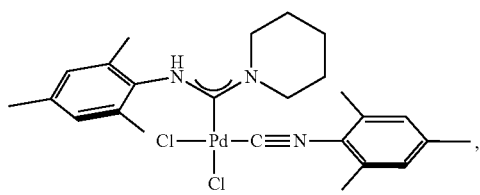

(ii). cis-[(2,4,6-(CH$_3$)$_3$C$_6$H$_2$NH)(NC$_4$H$_8$)methylidene] PdCl$_2$(CN-2,4,6-(CH$_3$)$_3$C$_6$H$_2$) having formula (Ib):

Formula (Ib)

(3)

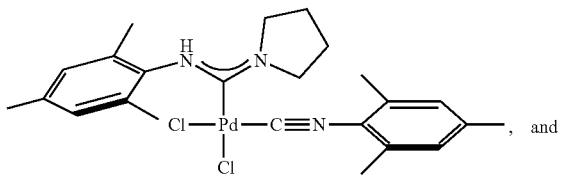, and (iii). cis-[(2,4,6-(CH$_3$)$_3$C$_6$H$_2$NH)(NC$_4$H$_8$O)methylidene] PdCl$_2$(CN-2,4,6-(CH$_3$)$_3$C$_6$H$_2$) having formula (Ic):

Formula (Ic)

(4)

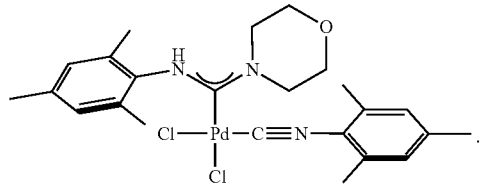.

2. A method of organic synthesis by a Hiyama coupling reaction comprising contacting an aryl iodide and a triethoxysilylalkyne with an acyclic diaminocarbene complex as claimed in claim 1.

3. A method of organic synthesis by a Hiyama alkynylation reaction between an aryl iodide and a triethoxysilylalkyne comprising contacting the aryl bromide and the triethoxysilylalkyne with an acyclic diaminocarbene complex as claimed in claim 1.

4. A method comprising Hiyama coupling comprising contacting 2-iodophenol and a triethoxysilylalkyne with an acyclic diaminocarbene complex as claimed in claim 1 to produce a coupling product, followed by cyclization of the coupling product to provide benzofuran compounds.

5. A one pot, tandem route method comprising a Hiyama alkynylation comprising contacting 2-iodophenol and a triethoxysilylalkyne with an acyclic diaminocarbene complex as claimed in claim 1 and a cyclization reaction to provide benzofuran compound.

* * * * *